(12) United States Patent
Usagawa

(10) Patent No.: US 9,228,973 B2
(45) Date of Patent: Jan. 5, 2016

(54) GAS SENSOR

(75) Inventor: Toshiyuki Usagawa, Saitama (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 13/508,082

(22) PCT Filed: Oct. 1, 2010

(86) PCT No.: PCT/JP2010/067272
§ 371 (c)(1),
(2), (4) Date: May 4, 2012

(87) PCT Pub. No.: WO2011/055605
PCT Pub. Date: May 12, 2011

(65) Prior Publication Data

US 2012/0217550 A1    Aug. 30, 2012

(30) Foreign Application Priority Data

Nov. 6, 2009    (JP) ................. 2009-254522

(51) Int. Cl.
*H01L 27/088* (2006.01)
*G01N 27/414* (2006.01)
*G01N 33/00* (2006.01)

(52) U.S. Cl.
CPC ........ *G01N 27/4141* (2013.01); *G01N 27/4148* (2013.01); *G01N 33/005* (2013.01)

(58) Field of Classification Search
CPC ............ G01N 27/4141; G01N 27/129; G01N 33/0036; G01N 33/005; H01L 29/7394; H01L 27/105; H01L 2224/48247; H01L 23/345; H05B 2203/013
See application file for complete search history.

(56) References Cited

U.S. PATENT DOCUMENTS

| | | |
|---|---|---|
| 5,434,102 A | 7/1995 | Wantanabe et al. |
| 5,723,171 A | 3/1998 | Cuchiaro et al. |

(Continued)

FOREIGN PATENT DOCUMENTS

| | | |
|---|---|---|
| JP | 06-58899 A | 3/1994 |
| JP | 06-242048 A | 9/1994 |

(Continued)

OTHER PUBLICATIONS

Yokosawa et al., "Hydrogen Gas Detection System Prototype with Wireless Sensor Networks", Fuel Cell, vol. 4, No. 4 (2005), p. 60-63.

(Continued)

*Primary Examiner* — Ori Nadav
*Assistant Examiner* — Ernest Allen, III
(74) *Attorney, Agent, or Firm* — Miles & Stockbridge P.C.

(57) ABSTRACT

A MISFET-type hydrogen gas sensor having low power consumption which can be operated for one year or longer at a low voltage power source (for example, 1.5 to 3 V) is achieved. A sensor FET is formed in a MEMS region 34 where a Si substrate 22 of a SOI substrate is bored, and a heater wiring 32 is arranged so as to be folded between a Pi-Ti—O gate 28 and a source electrode 31S of the sensor FET and between the Pt—Ti—O gate 28 and a drain electrode 31D thereof, respectively. Further, a plurality of through-holes 36 obtained by removing a protective film so as to expose an embedded insulation layer of the SOI substrate are formed in a region where an intrinsic FET region 35 where the sensor FET is formed does not overlap with the MEMS region 34 and except for bridge regions 90, 90S, 90G, and 90H where lead-out wirings 20S, 20D, 20G, and 20H are formed and except for reinforced regions 91.

18 Claims, 20 Drawing Sheets

(56) References Cited

U.S. PATENT DOCUMENTS

| | | | |
|---|---|---|---|
| 5,747,839 A * | 5/1998 | Hammond et al. | 257/253 |
| 6,111,280 A * | 8/2000 | Gardner et al. | 257/253 |
| 6,267,470 B1 * | 7/2001 | Watanabe | 347/59 |
| 7,176,700 B2 | 2/2007 | Itakura et al. | |
| 2003/0007319 A1 * | 1/2003 | Zhang et al. | 361/523 |
| 2004/0075140 A1 * | 4/2004 | Baltes et al. | 257/347 |
| 2004/0195096 A1 * | 10/2004 | Tsamis et al. | 204/426 |
| 2005/0097941 A1 | 5/2005 | Sandvik et al. | |
| 2006/0185980 A1 | 8/2006 | Fukuda | |
| 2006/0277977 A1 * | 12/2006 | Kahn et al. | 73/53.01 |
| 2008/0054382 A1 * | 3/2008 | Stetter | 257/414 |
| 2008/0064086 A1 * | 3/2008 | Lee et al. | 435/289.1 |
| 2009/0256161 A1 | 10/2009 | Sekimoto et al. | |
| 2011/0254104 A1 * | 10/2011 | Maeda | 257/369 |

FOREIGN PATENT DOCUMENTS

| | | | |
|---|---|---|---|
| JP | 07-020555 U | | 4/1995 |
| JP | 9-159633 A | | 6/1997 |
| JP | 9-318569 A | | 12/1997 |
| JP | 11-295254 A | | 10/1999 |
| JP | 11295254 A | * | 10/1999 |
| JP | 2000-230859 A | | 8/2000 |
| JP | 2000230859 A | * | 8/2000 |
| JP | 2001-505367 A | | 4/2001 |
| JP | 2001-235442 A | | 8/2001 |
| JP | 2002-071611 A | | 3/2002 |
| JP | 2005-502480 A | | 1/2005 |
| JP | 2006-226860 A | | 8/2006 |
| JP | 2006-234576 A | | 9/2006 |
| JP | 2007-512514 A | | 5/2007 |
| JP | 2008-60430 A | | 3/2008 |

OTHER PUBLICATIONS

Yokosawa et al., "Hydrogen-Gas Detection System and its Functions to make Each Sensor Wireless", Transactions on Electrical and Electronic Engineering, IEEJ trans 2008, vol. 3, pp. 229-235.

Usagawa et al., "Developments and Lifetime Evaluations for Low Power Si-MOSFET Hydrogen Gas Sensors", Fuel Cell, vol. 8, No. 3, (2009), pp. 88-96.

Fukui, "Now and Future in Hydrogen Gas Sensors", Surface Technology, vol. 57, No. 4 (2006), pp. 244-249.

Choi et al., "No Blister Formation Pd/Pt Double Metal Gate MISFET Hydrogen Sensors", IEEE Electron Device Letters, vol. EDL-5, No. 1, Jan. 1984, pp. 14-15.

Morita et al., "Langmuir analysis on hydrogen gas response of palladium-gate FET", Sensors and Actuators, B33 (1996), pp. 96-99.

New Energy and Industrial Technology Development Organization, Suiso Kiso Bussei no Kenkyu, Mar. 2008, pp. 3.494-3.496.

T. Usagawa et al., Reliable Low Power Si-MOSFET Hydrogen Sensors, Chemical Sensors, vol. 24, Supplemental B, pp. 58-60 (3008).

Office Action (Notification of Reasons for Refusal) dated Oct. 8, 2013 in Japanese Patent Application No. 2011-539321.

* cited by examiner

GAS SENSOR

TECHNICAL FIELD

The present invention relates to a gas sensor, and more particularly, the present invention relates to a technique effectively applied to a structure of a hydrogen gas sensor with low power consumption for detecting hydrogen gas and a method of controlling a threshold voltage of the hydrogen gas sensor.

BACKGROUND ART

Hydrogen gas has properties of odor free and low ignition energy which results in large explosion power. Therefore, in order to exactly monitor leakage of hydrogen gas in a pipeline for city gas or others and detect the leakage of hydrogen gas in an industrial hydrogen gas line, usability of a system in which a lot of small-sized hydrogen gas sensors are arranged to monitor leakage locations has been reviewed. For example, in a hydrogen concentration which is several percentages of a concentration of explosion limit, a hydrogen gas sensor which can detect hydrogen gas at a high response speed (for example, in a range of 1 to 3 seconds) is required. An idea of such a monitoring system is described in, for example, Fuel Cell, VOL, 4, No. 4, 2005, p. 60-63 (Non-Patent Document 1). In order to achieve such a monitoring system, for the hydrogen gas sensor, it is desired to respond to a hydrogen concentration which is 10% of 100 ppm at a high speed and to be low power consumption, small sized, and low cost. Also in monitoring the hydrogen leakage in fuel cell vehicle or hydrogen vehicle, a hydrogen gas sensor with low power consumption is useful.

Incidentally, there is a lithium cell (lithium battery) as one of batteries which can take the most current capacity recently. The lithium cell has a risk of ignition. However, in a case of up to two of them, it is legally established that it is not required to take a countermeasure based on a specific mounting structure for firing safety measures. When a hydrogen gas sensor is operated by using two lithium batteries with high current capacity (for example, a voltage of 3 V and a current capacity of 2.6 Ah) of the lithium cells, if power consumption is 1 mW, continuous operation of the hydrogen gas sensor for about 650 days is possible. That is, as long as the operation for one year, power consumption up to 1.78 mW is allowed. Further, when a hydrogen gas sensor is operated by using one small-sized button cell for a mobile device, even if it is a lithium cell with relatively large capacity, a voltage is 3 V but a current capacity is such small as 0.61 Ah. Therefore, in order to operate the hydrogen gas sensor for one year or longer, an idea for further reduction in the power consumption is required. The power consumption of the hydrogen gas sensor is defined mainly by a sensor unit and an interface circuit. The power consumption of the interface circuit can be reduced by configuring the interface circuit to be an IC.

As a hydrogen gas sensor whose mass production is easy and which has a property of low power operation with using Si semiconductor, a hydrogen gas sensor of a Si-MISFET (Metal Insulator Semiconductor Field Effect Transistor) type has been proposed. However, even in the Si-MISFET-type hydrogen gas sensor, if the high-speed response is required, it is required to heat the Si-MISFET-type hydrogen gas sensor at 100 to 200° C.

The present inventor has achieved the power consumption of about 100 mW in the Si-MISFET-type hydrogen gas sensor on which a sensor chip having a size of 2 mm square is mounted (see in, for example, Fuel Cell, Vol. 8, No. 3, (2009), p. 88 to 96 (Non-Patent Document 2)). However, as described above, in the cell operation, further reduction in the power consumption is required.

In the Si-MISFET-type hydrogen gas sensor in the above-described Non-Patent Document 2, a sensor MISFET, a reference MISFET, and a PN-junction-type diode for measuring the temperature are surrounded on a surface of the sensor chip by a heater wiring made of metal, and the whole sensor chip having a flat dimension of 2 mm×2 mm and a thickness of 0.4 mm is heated at 100 to 150° C. In this case, a lot of lead wires are used.

Further, as a substrate for the sensor chip, a Si substrate made of monocrystalline Si is generally used. However, the Si substrate has a thermal conductivity of 148 W/(m·° C.). Therefore, as a technique for the power reduction, an MEMS (Micro Electro Mechanical Systems) structure is known, in which a Si substrate is bored and a heater is formed in the bored region. For example, U.S. Patent Application Laid-Open Publication No. 2004/0075140 (Patent Document 1) discloses a technique in which, a Si substrate is bored, an insulator such as a $Si_3N_4$ film or a $SiO_2$ film having low thermal conductivity is thinly formed in the bored portion, a flammable gas sensor with using a thin film such as a $SnO_2$ film in the portion and a heater formed of a resistor body are formed and heated at about 400° C. However, in this example, the MISFET is not formed in the bored portion.

Further, for example, U.S. Pat. No. 6,111,280 (Patent Document 2) discloses a flammable gas sensor in which, an SOI (Silicon On Isolator) substrate is used, a Si-MISFET formed in a bored region in a Si substrate is used as a heater, and a sensitive membrane (for example, an $SnO_2$ film) is arranged on the Si-MISFET to be used as a gas sensor film. Further, it discloses a hydrogen gas sensor in which, a sensitive film made of metal oxide to which a material having catalytic function is doped is formed on a gate insulating film of the Si-MISFET formed in the bored region in the Si substrate, and a Pt electrode is formed on the sensitive film. Further, it also discloses to form a heater made of a resistor body is formed on a rear surface of the $SiO_2$ film in the bored region in the Si substrate and to heat the Si-MISFET. However, in such a structure of a hydrogen gas sensor, a manufacturing step such as performing a plurality of lithography processes to the rear surface of the SOI substrate having concave-convex surfaces is used after a lithography process to a front surface of the SOI substrate.

Meanwhile, if the low power consumption cannot be sufficiently achieved by continuous current flow, an intermittent operation method is effective. The intermittent operation method can be used, in which, heating time is represented as "$\tau_1$" and heating stop time is represented as "$\tau_2$", and the power consumption for heating can be effectively reduced by a duty ratio "$(\tau_1/(\tau_1+\tau_2))$". This intermittent operation method is effective when a time constant determined by the product of a thermal capacity of a targeted region with a thermal resistance connected to the targeted region is sufficiently shorter than the heating time $\tau_1$ and the heating stop time $\tau_2$. In this method, if the heating stop time $\tau_2$ is long, the power consumption can be reduced with no limit in principle. However, performance of the detection of gas leakage is reduced.

Because of limitation of the response speed of the conventional hydrogen gas sensor, it is determined in current regulations that the response speed of the hydrogen gas sensor is 30 seconds or shorter. Therefore, if a hydrogen gas sensor with a high response speed (for example, about one second) is provided, the explosion by the leakage of hydrogen gas can be prevented without damaging safety even in such an intermittent operation in which heating is performed for 2 seconds by the heater, and then, heating is stopped for 28 seconds. Therefore, a lower limit of the duty ratio is about 1/14. That is, when two lithium cells which are not regulated legally are used for, for example, a cordless monitoring system or a sensor node of a wireless monitoring system in the above-described Non-Patent Document 1, the lower limit of the power consumption is expressed as 25 mW×(1/14)≅1.78 mW. Therefore, it is considered that an upper limit of the power consumption in the heater heating for which the operation for one year can be ensured is about 25 mW.

In the Si-MISFET-type hydrogen gas sensor, on which the sensor chip having a size of 2 mm square (in which a thickness of the Si substrate is 0.4 mm) is mounted, achieved in the above-described Non-Patent Document 2, the thermal capacity of the sensor chip whose size is 2 mm square is such large as about 270 μW-second/° C. Therefore, when a chip temperature is raised from an environmental temperature (for example, −35° C.) to about 150° C., the arrival time t0 to the temperature is obtained by the quotient of the product of the thermal capacity C with a temperature difference ΔT and the heater power Pow supplied, and it takes about 1 second in 100 mW and takes about 100 seconds in 1 mW. In such a hydrogen gas sensor, when the heater is continuously operated, the arrival time t0 does not become a problem since it does not rapidly change the sensor temperature. However, when the intermittent operation of the heater is achieved, it becomes a large interruption. That is, in the existing publicly-known techniques, there is no hydrogen gas sensor equipped with a heater which can be used by a cell for a long period.

Further, an installation environmental temperature of the hydrogen gas sensor used is in a wide temperature range from a low temperature of −50° C. to a high temperature of 70° C. in some cases, and the installation is required in some cases in a place where the environmental temperature in the installation changes every day or every year. For example, in a catalytic-combustion-type hydrogen gas sensor described in, for example, Kiyoshi Fukui, Surface Technology, Vol. 57, No. 4, (2006), p. 244 to 249 (Non-Patent Document 3) or others, the problem of temperature change is solved by using a temperature compensation device, that is, a balance circuit (a Wheatstone bridge circuit or others) having a structure equivalent to that of the hydrogen gas sensor.

Further, in a Pt-gate Si-MISFET-type hydrogen gas sensor with using Pt for a gate, there are problems such that reliability for a long term cannot be guaranteed because an adhesive property between Pt and oxide such as $SiO_2$ is poor and that a Pt film is partially peeled off, which results in contamination of a manufacturing apparatus by the peeled-off Pt film in a working process for manufacturing the Si-MISFET. Therefore, when Pt is used, the adhesive property is maintained by inserting barrier metal such as Ti, Mo, or W between Pt and $SiO_2$, so that the contamination due to the peeling off is avoided. However, when the hydrogen gas sensor is operated, if such a barrier metal layer exists, the hydrogen gas is blocked or stored by the barrier metal layer, and therefore, there is a problem that the sensor cannot be used as the hydrogen gas sensor because the hydrogen gas sensor does not react with the hydrogen gas at all or the hydrogen response speed is significantly low (see in, for example, S. Y. Choi, et. al, IEEE Electron Device Letters, EDL-5, 14-15 (1984) (Non-Patent Document 4)).

In a Pd-gate Si-MISFET-type hydrogen gas sensor obtained by forming Pd catalytic on a gate insulating film ($SiO_2$ film) by a sputtering method, such an effect that thermal treatment at 100° C. with 1% air-diluted hydrogen gas by significantly shorten the response time for the 1% air-diluted hydrogen gas from 50 hours to 55 seconds has been found (see in, for example, Y. Morita, et. al, Sensors and Actuators, B33, 96-99 (1996) (Non-Patent Document 5)). Note that, when irradiation of the 1% air-diluted hydrogen gas is stopped, hydrogen response intensity slightly remains so that the time required for the stop of the hydrogen response is about 655 seconds. The above-described Non-Patent Document 5 reports that, while threshold voltages Vth of an n-channel-type MISFET and a p-channel-type MISFET are 1.3 V and −0.6 V before hydrogen annealing, respectively, both of the threshold voltages obtained after the thermal treatment at 100° C. with the 1%-air diluted hydrogen gas are changed to 0.2 V.

PRIOR ART DOCUMENTS

Patent Documents

PATENT DOCUMENT 1: U.S. Patent Application Laid-Open Publication No. 2004/0075140
PATENT DOCUMENT 2: U.S. Pat. No. 6,111,280

Non-Patent Documents

Non-PATENT DOCUMENT 1: Yokosawa and other three, Fuel Cell, Vol. 4, No. 4, (2005), p. 60 to 63
Non-PATENT DOCUMENT 2: Usagawa and other three, Fuel Cell, Vol. 8, No. 3, (2009), p. 88 to 96
Non-PATENT DOCUMENT 3: Kiyoshi Fukui, Surface Technology, Vol. 57, No. 4, (2006), p. 244 to 249
Non-PATENT DOCUMENT 4: S. Y. Choi, et.al, IEEE Electron Device Letters, EDL-5, 14-15, (1984)
Non-PATENT DOCUMENT 5: Y. Morita, et.al, Sensors and Actuators, B33, 96-99, (1996)

DISCLOSURE OF THE INVENTION

Problems to be Solved by the Invention

The hydrogen gas sensor with the low power consumption can be achieved by, for example, the Si-MISFET-type hydrogen gas sensor disclosed in the above-described Patent Document 2. However, there is such a problem that its manufacturing process is complicated, which results in low manufacturing yield. Further, there is such a problem that it is difficult to achieve the hydrogen gas sensor with the low power consumption which allows the operation thereof for one year or longer by a low-voltage power source (for example, 1.5 to 3 V) using a cell or others (First Problem).

A preferred aim of the present invention is to provide a technique capable of easily achieving a Si-MISFET-type hydrogen gas sensor with low power consumption which allows operation thereof for one year or longer by a low-voltage power source (for example, 1.5 to 3 V).

Further, another preferred aim thereof is to provide a technique capable of improving controllability of a threshold voltage of a sensor MISFET of a Si-MISFET-type hydrogen gas sensor (Second Problem) and achieving a Si-MISFET-type hydrogen gas sensor in which an operation temperature can be maintained constant against change in an environmental temperature without forming a temperature compensation device (Third Problem).

The above and other preferred aims and novel characteristics of the present invention will be apparent from the description of the present specification and the accompanying drawings.

Means for Solving the Problems

The typical ones of the inventions disclosed in the present application will be briefly described as follows.

An embodiment of the present invention describes a hydrogen gas sensor including: a sensor chip having a sensor MISFET and a heater formed at a heater region on a main surface of a substrate; a mounting substrate on which the sensor chip is mounted; and a heat insulation material inserted between the sensor chip and the mounting substrate. And, on the main surface of the substrate of the sensor chip, a pad electrode is formed so as to be connected to the heater via a lead-out wiring, a lead terminal used for connection to an outside is formed so as to penetrate through the mounting substrate, and the pad electrode and the lead terminal are connected to each other by a lead wire. The sensor MISFIT includes a catalytic metal gate, a source electrode, and a drain electrode and, and a heater is arranged on a plane that extends between the source electrode and the drain electrode and has a first portion at one side of the catalytic metal gate and a second portion at an opposite side of the catalytic metal gate and has a gap region between the first portion and the second portion. The heater is provided at a height position higher than a height position of the catalytic metal gate in a direction perpendicular to the plane on which the heater is arranged.

When it is assumed that a thermal resistance obtained from a heater region where the heater is formed to the mounting substrate so as to interpose the sensor chip and the heat insulation material therebetween is represented as "$R_D$", that a total thermal resistance of a thermal resistance from the heater region to the pad electrode and a thermal resistance or the lead wire is represented as "$R_L$", that a radius of a circle having the same area size as a surface area of the heater region is represented as "$r_A$", that a thermal conductivity of atmosphere gas generated by the heating of the heater is represented as "$\lambda$", that a difference between a set temperature of the heater region and an environmentally-assumed lowest temperature in installation is represented as a temperature difference "$\Delta Tmax$", and that a heater maximum power supplied to the heater which is determined by an electric resistance of the heater at the set temperature and a power source voltage is represented as "Powmax", if the heater maximum power Powmax is 25 mW or less, but greater than zero the thermal resistances $R_D$ and $R_L$ and the surface area of the heater region are set so as to satisfy a relationship of "$Powmax/\Delta Tmax > 1/R_D + 1/R_L + 4\pi\lambda \cdot r_A$".

Effects of the Invention

The effects obtained by an embodiment of typical aspects of the present invention disclosed in the present application will be briefly described below.

A Si-MISFET-type hydrogen gas sensor with low power consumption which allows operation thereof for one year or longer by a low-voltage power source (for example, 1.5 to 3 V) can be achieved.

BRIEF DESCRIPTIONS OF THE DRAWINGS

Figure 4A:
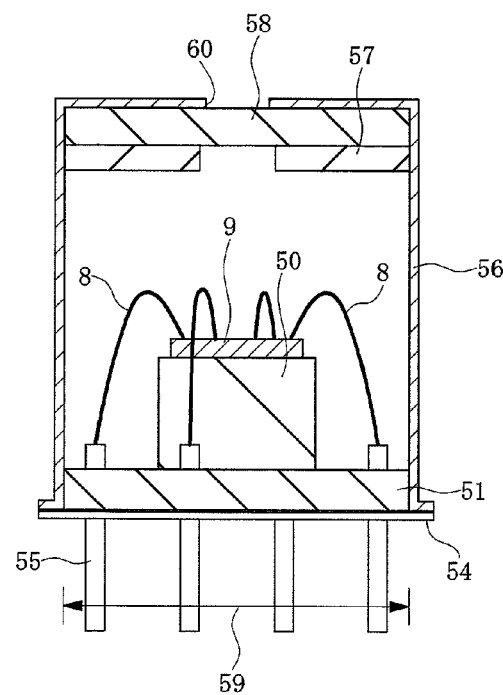
Figure 4B:
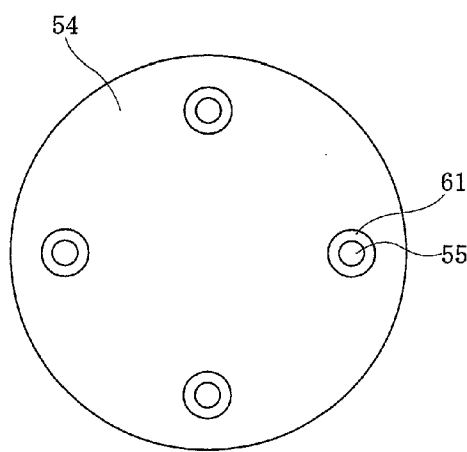
Figure 4C:
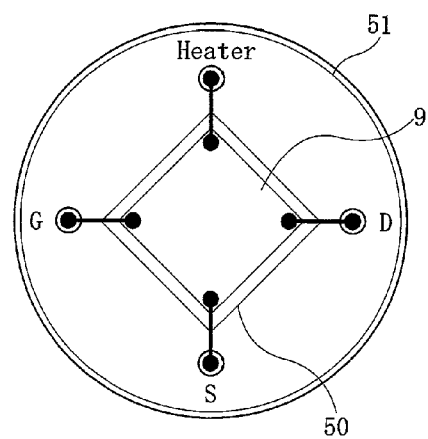
Figure 5A:
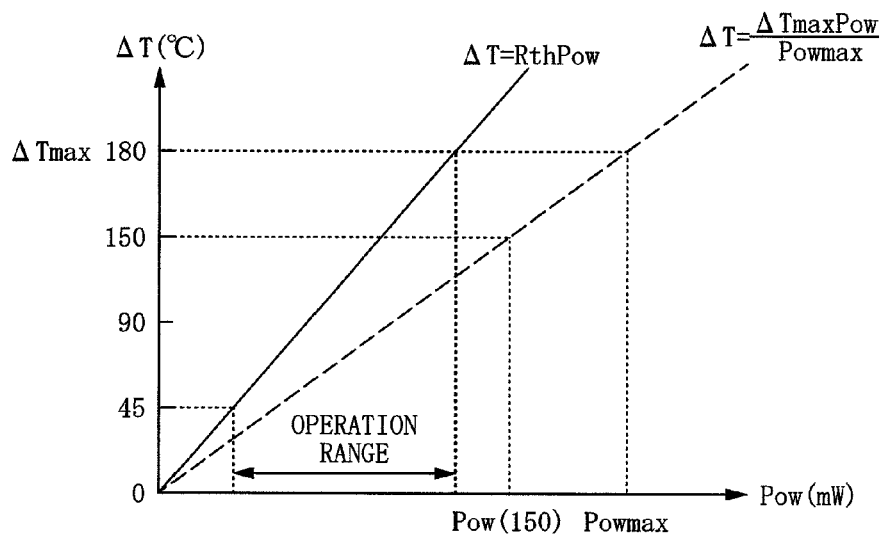
Figure 5B:
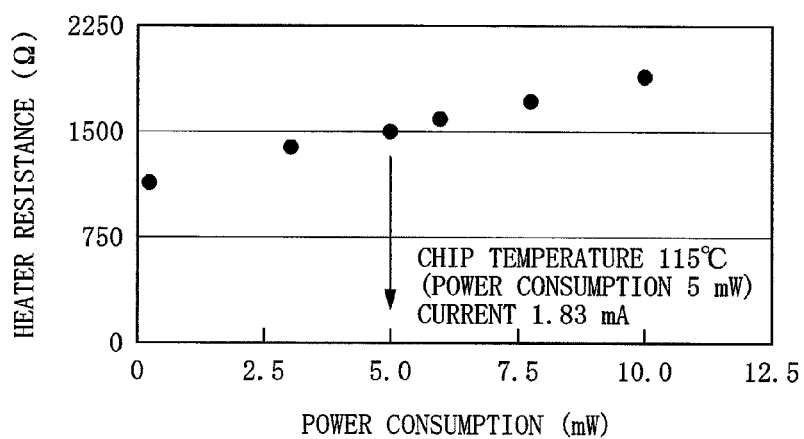
Figure 6A:
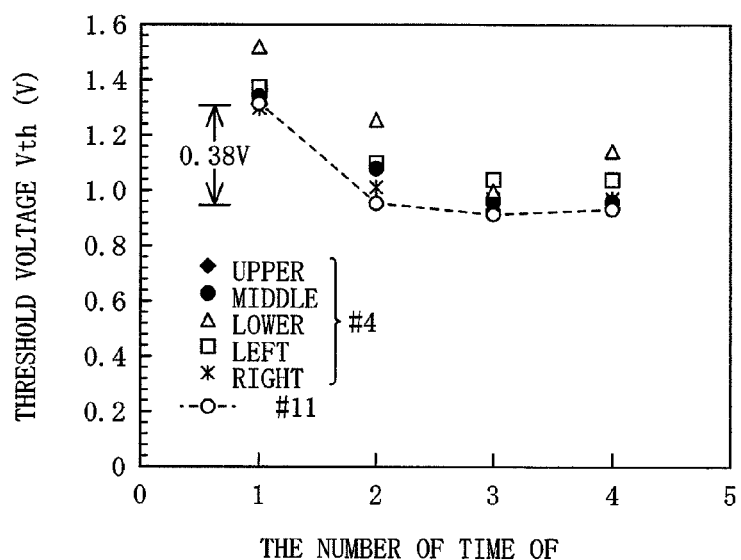
Figure 6B:
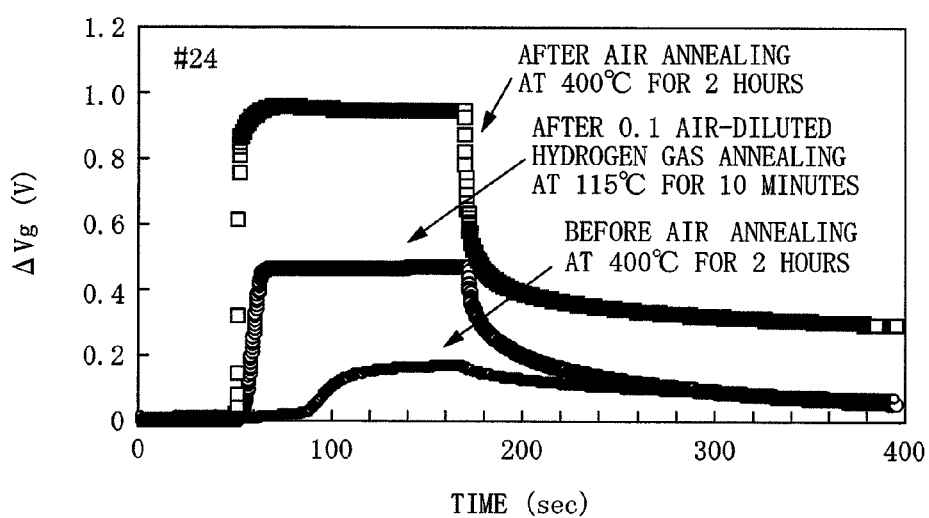
Figure 7A:
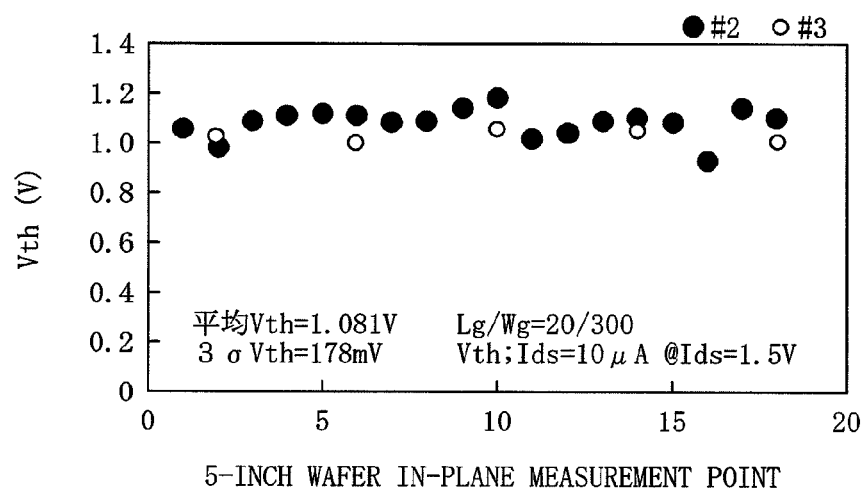
Figure 7B:
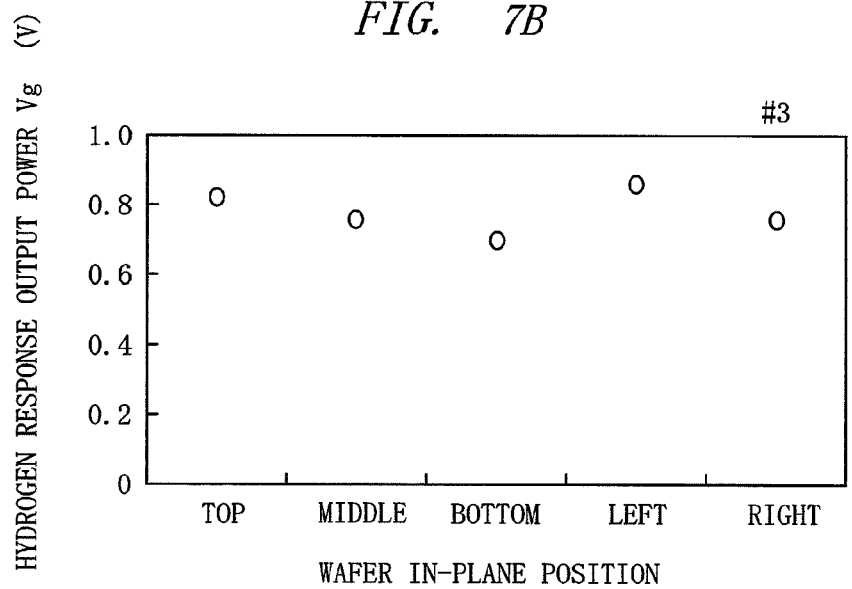
Figure 8A:
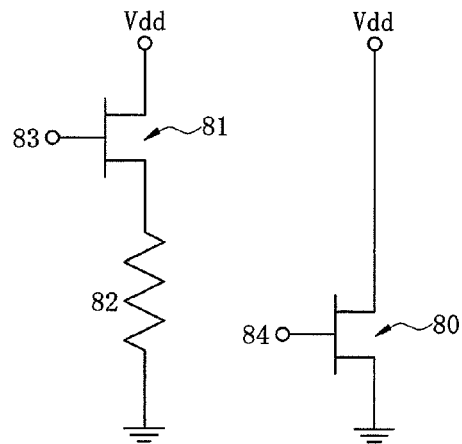
Figure 8B:
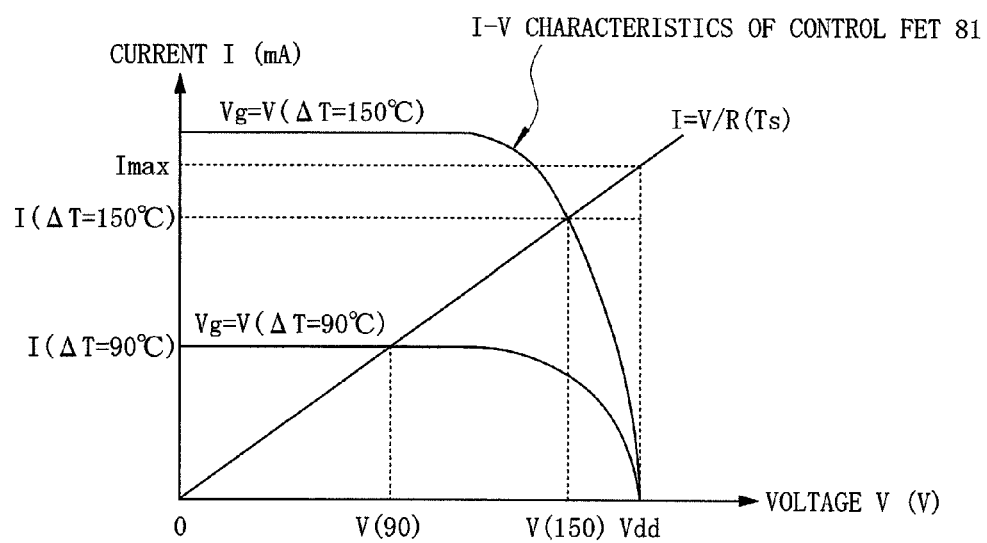
Figure 9:
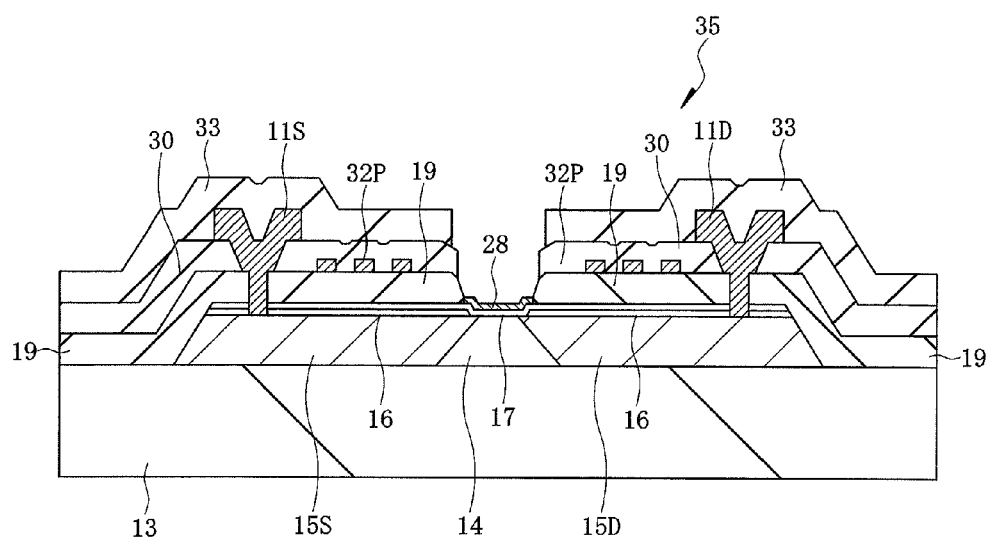
Figure 11:
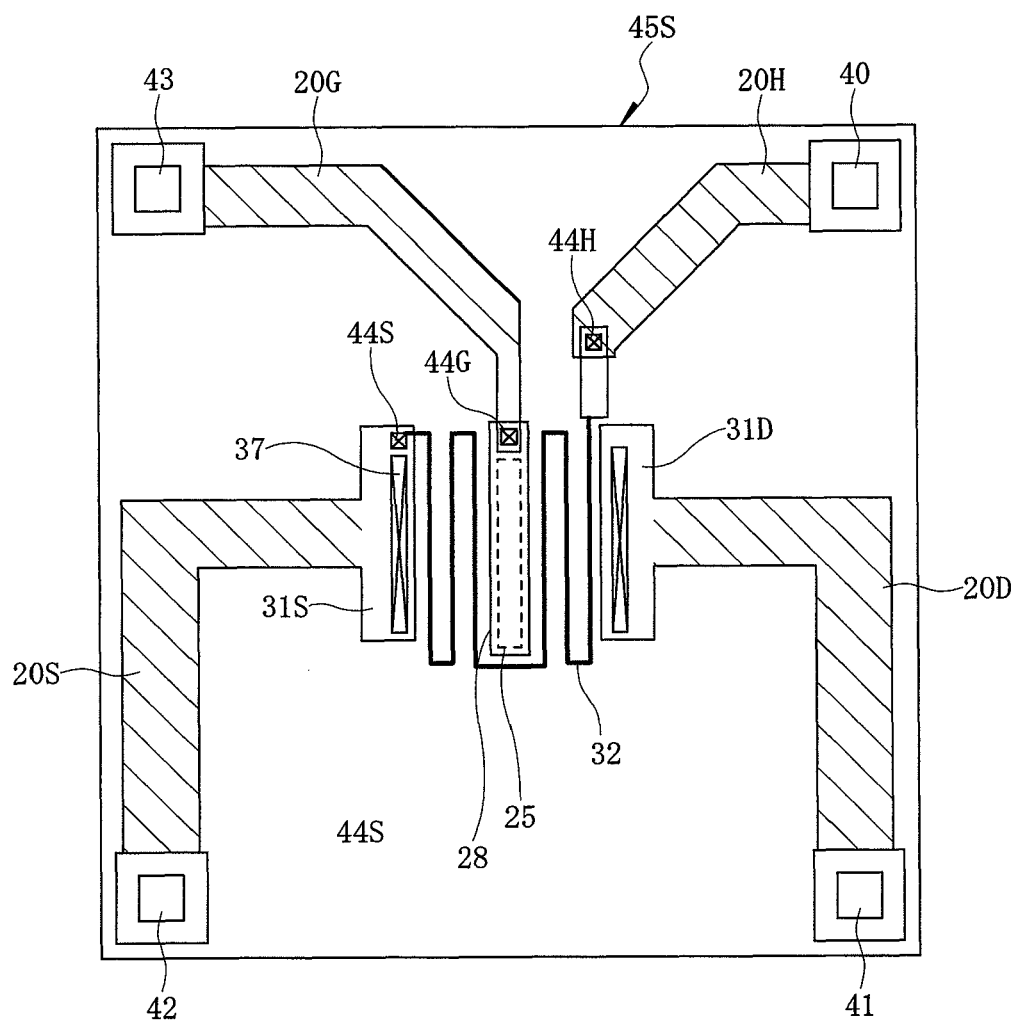
Figure 12:
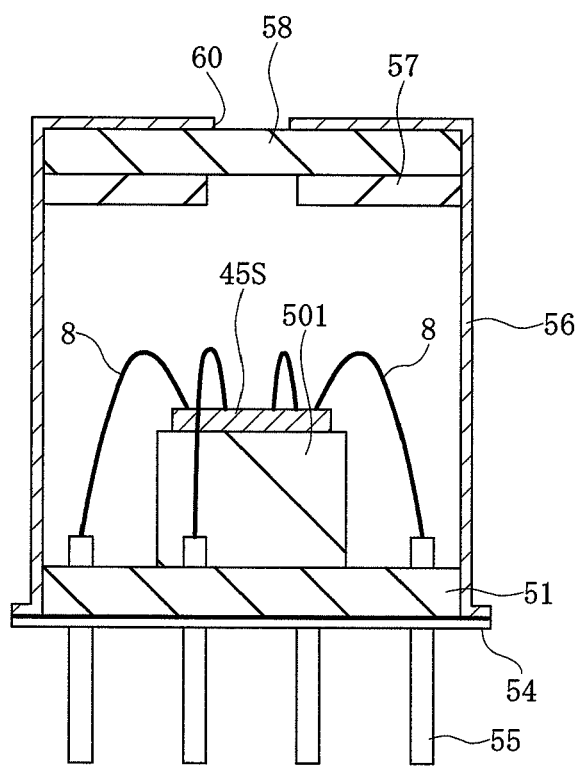
Figure 13:
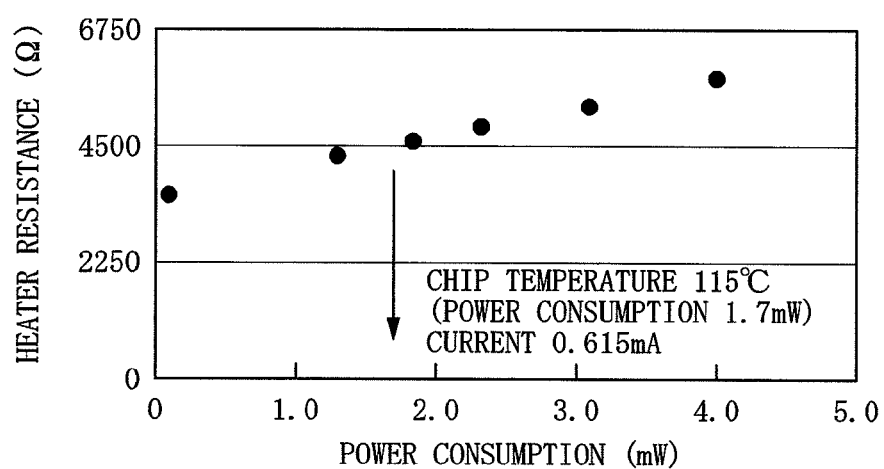
Figure 14:
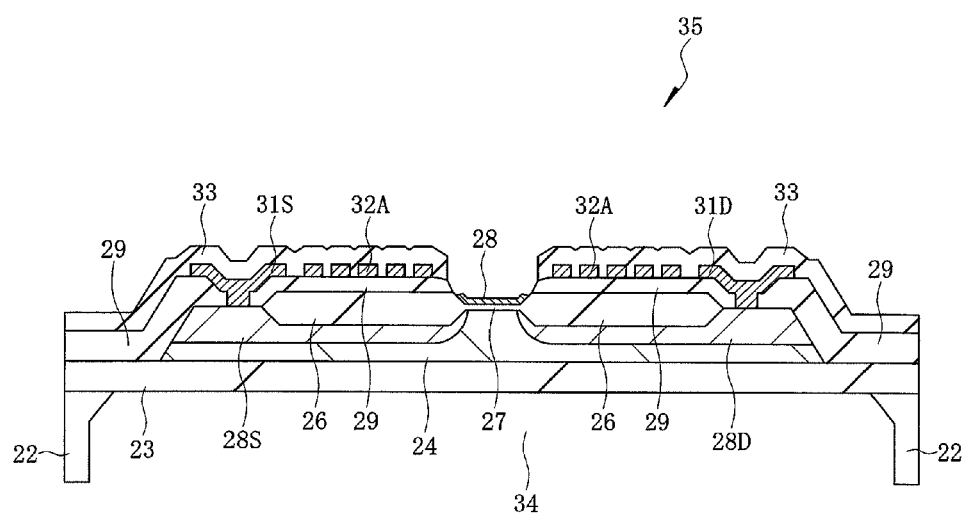
Figure 15:
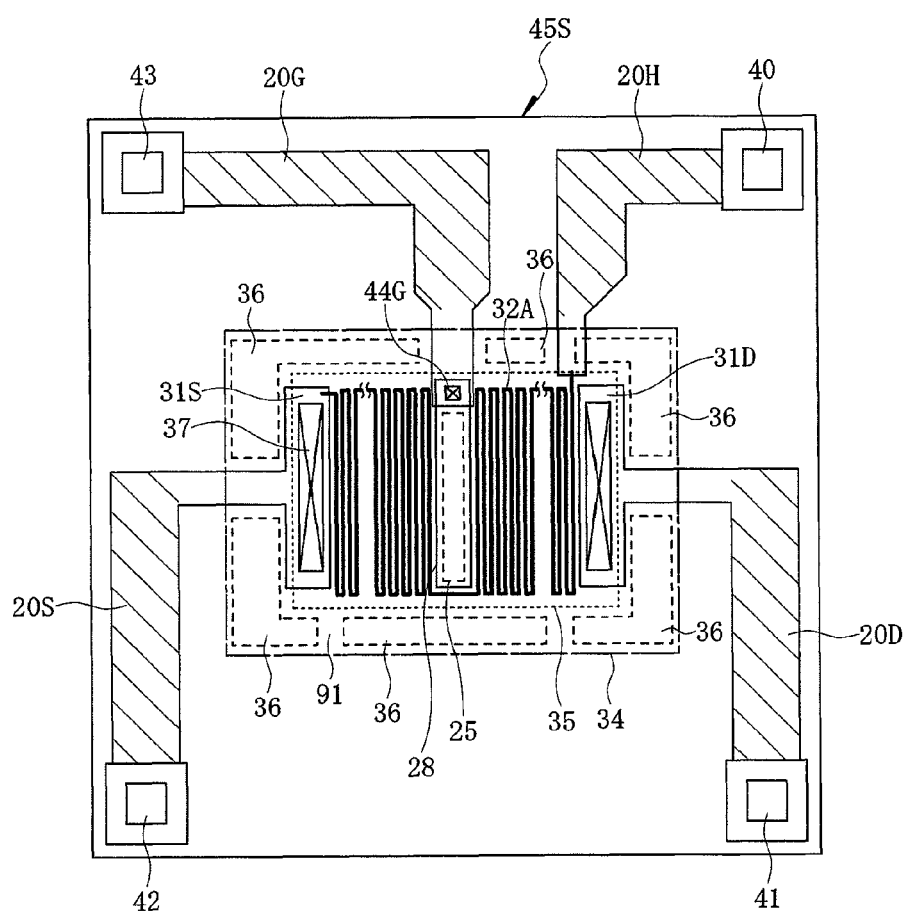
Figure 16:
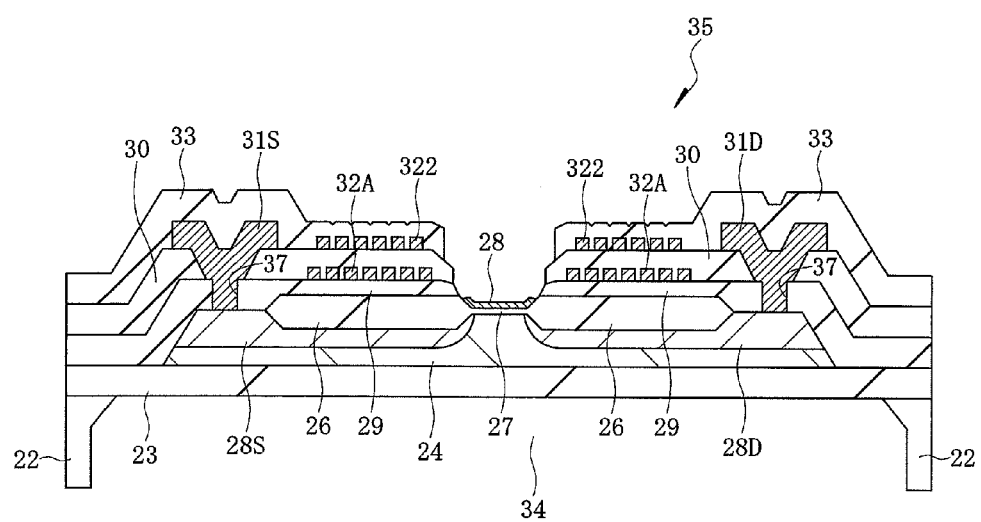
Figure 17:
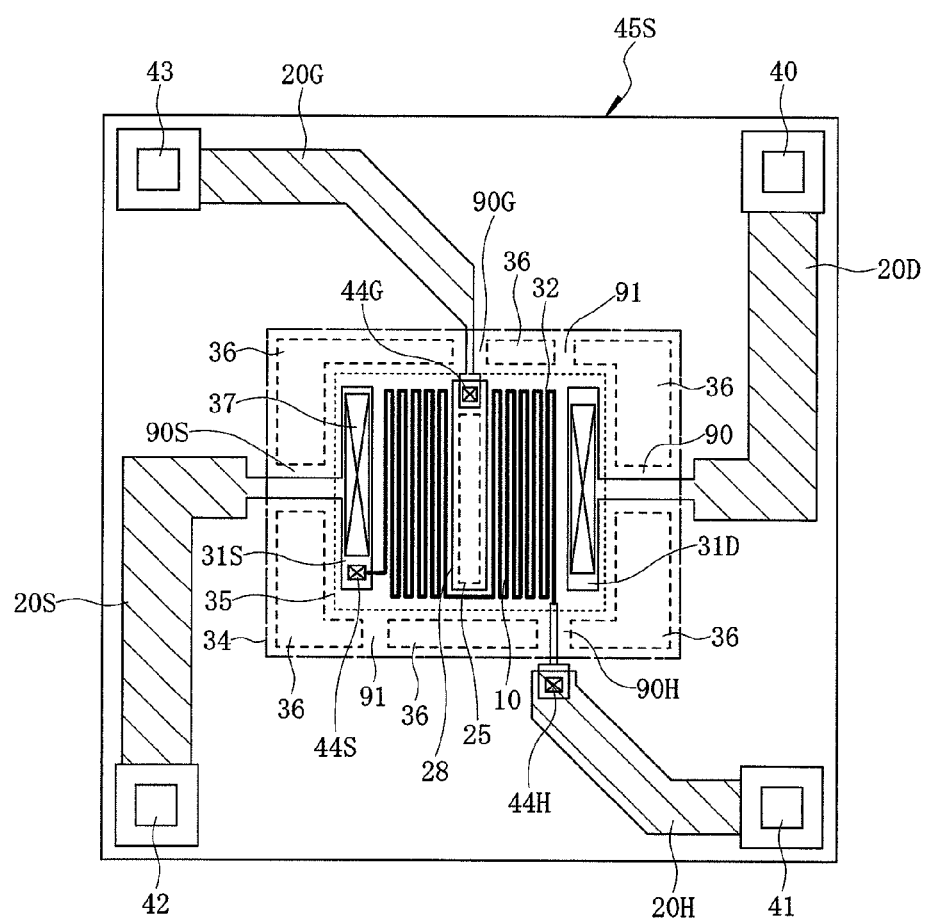
Figure 18:
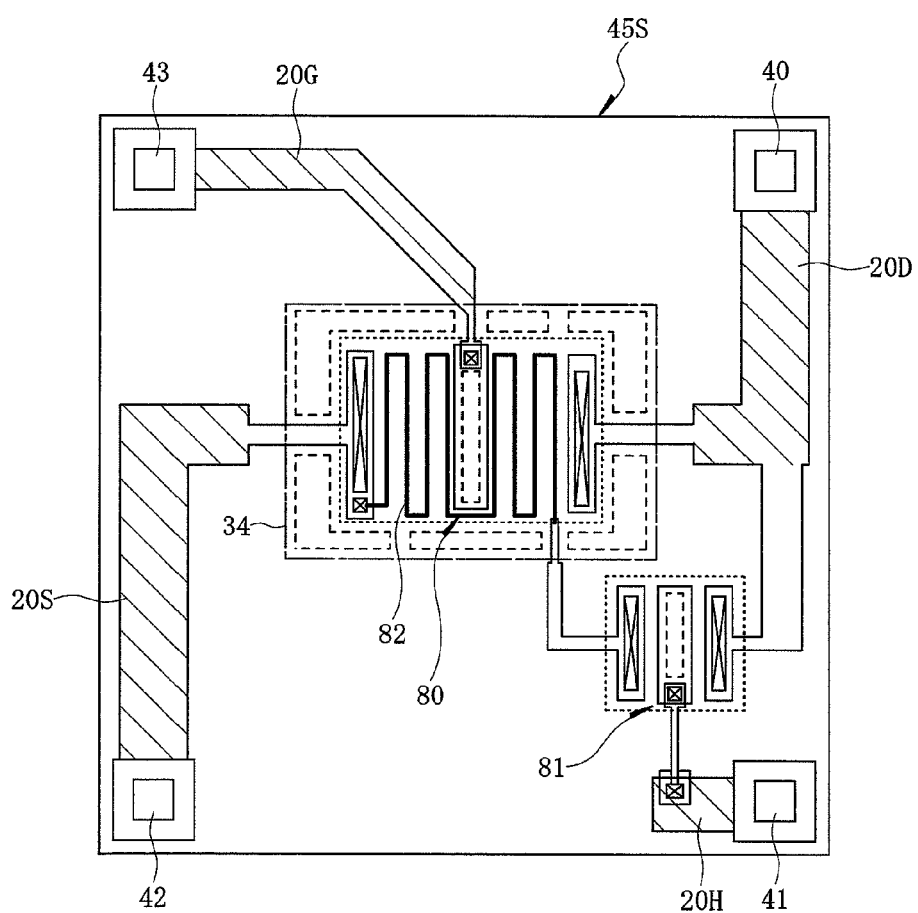
Figure 19:
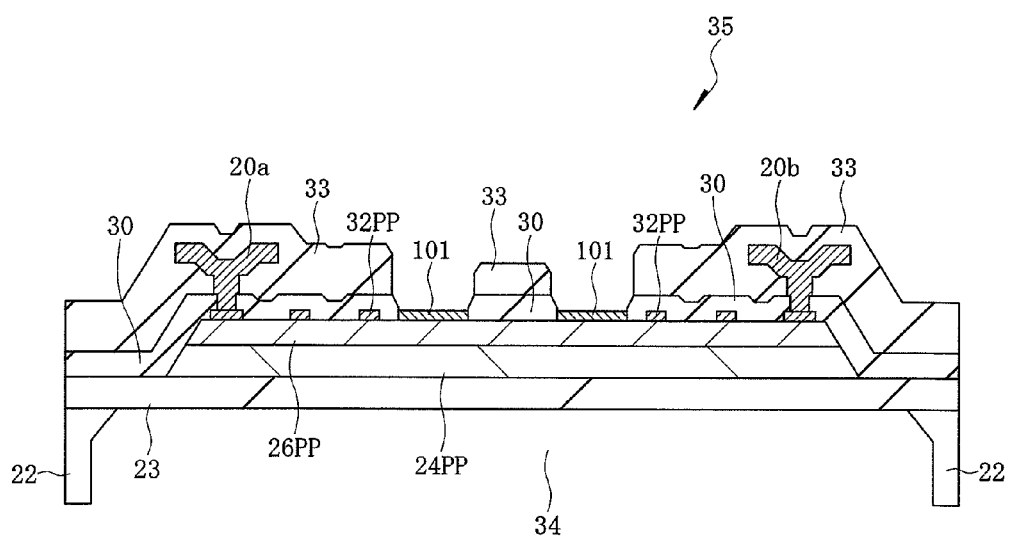
Figure 20:
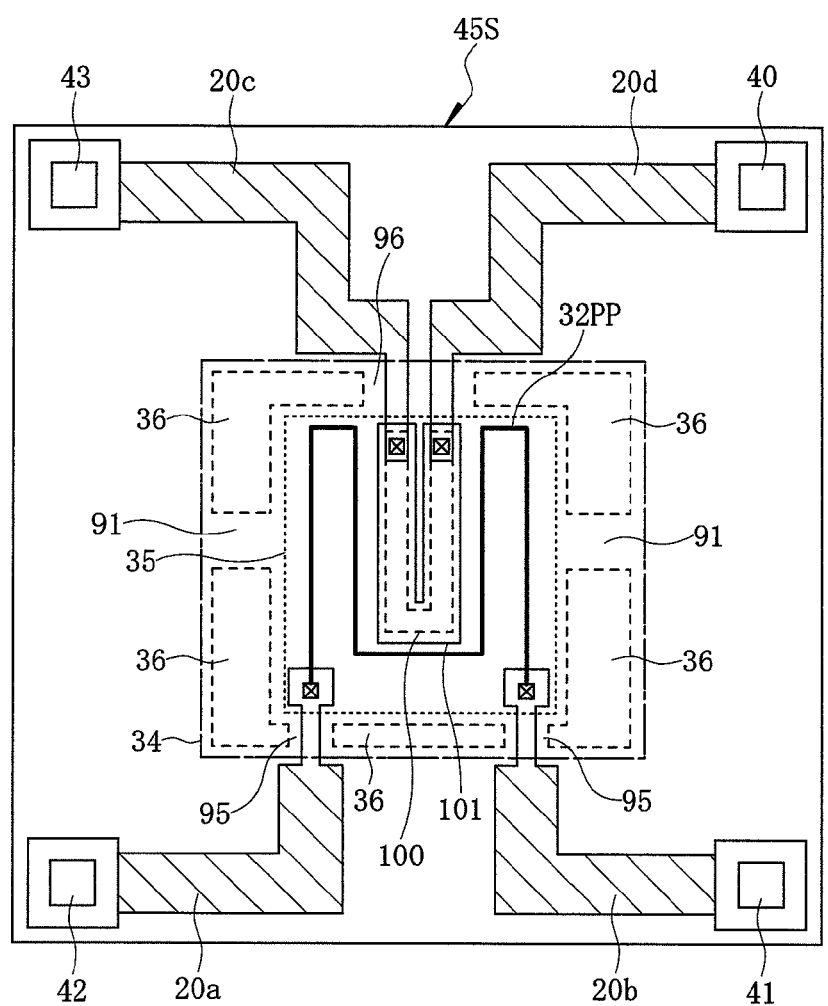

FIGS. 4A, 4B and 4C are a cross-sectional schematic view of a hydrogen gas sensor on which the sensor chip according to the first embodiment of the present invention is mounted, a rear surface schematic view of a stem base according to the first embodiment of the present invention, and a front surface schematic view of the stem base according to the first embodiment of the present invention, respectively;

FIGS. 5A and 5B are a graph diagram for explaining power consumption characteristics according to the first embodiment of the present invention and a graph diagram for explaining heater power consumption characteristics of the hydrogen gas sensor according to the first embodiment of the present invention, respectively;

FIGS. 6A and 6B are a graph diagram for explaining controllability of a threshold voltage according to the first embodiment of the present invention and a graph diagram for explaining time response of a hydrogen response output according to the first embodiment of the present invention, respectively;

FIGS. 7A and 7B are a wafer in-plane distribution diagram of a threshold voltage for explaining a wafer in-plane distribution of a threshold voltage and repeatability thereof according to the first embodiment of the present invention and a diagram for explaining a wafer in-plane distribution of a hydrogen response output according to the first embodiment of the present invention;

FIGS. 8A and 8B are a control circuit diagram according to the first embodiment of the present invention and a graph diagram for explaining an operation (current-voltage characteristics) of the control circuit according to the first embodiment of the present invention, respectively;

FIG. 9 is a cross-sectional view of a principal part of a sensor MISFET, in which polysilicon formed on a glass substrate is used for a channel layer, according to a second embodiment of the present invention;

FIGS. 10A to 10D are cross-sectional views of a principal part illustrating a method of manufacturing the sensor MISFET according to the second embodiment of the present invention;

FIG. 11 is a plan view of a principal part of a sensor chip according to the second embodiment of the present invention;

FIG. 12 is a cross-sectional schematic view of a hydrogen gas sensor on which the sensor chip according to the second embodiment of the present invention is mounted, FIG. 13 is a graph diagram for explaining heater power consumption characteristics of a hydrogen gas sensor according to the second embodiment of the present invention;

FIG. 14 is a cross-sectional view of a principal part of a sensor MISFET according to a third embodiment of the present invention;

FIG. 15 is a plan view of a principal part of a sensor chip according to the third embodiment of the present invention;

FIG. 16 is a cross-sectional view of a principal part of a sensor MISFET according to another example of the third embodiment of the present invention;

FIG. 17 is a plan view of a principal part of a sensor chip according to another example of the third embodiment of the present invention;

FIG. 18 is a plan view of a principal part of a sensor chip according to a fourth embodiment of the present invention;

FIG. 19 is a plan view of a principal part of a flammable gas sensor according to a fifth embodiment of the present invention; and FIG. 20 is a plan view of a principal part of a sensor chip according to the fifth embodiment of the present invention.

BEST MODE FOR CARRYING OUT THE INVENTION

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof.

Also, in the embodiments described below, when referring to the number of elements (including number of pieces, values, amount, range, and the like), the number of the elements is not limited to a specific number unless otherwise stated or except the case where the number is apparently limited to a specific number in principle. The number larger or smaller than the specified number is also applicable. Further, in the embodiments described below, it goes without saying that the components (including element steps) are not always indispensable unless otherwise stated or except the case where the components are apparently indispensable in principle. Similarly, in the embodiments described below, when the shape of the components, positional relationship thereof, and the like are mentioned, the substantially approximate and similar shapes and the like are included therein unless otherwise stated or except the case where it is conceivable that they are apparently excluded in principle. The same goes for the numerical value and the range described above.

Also, in some drawings used in the embodiments described below, hatching is used even in a plan view so as to make the drawings easy to see. Further, in the following embodiments, a metal insulator semiconductor field effect transistor (MISFET) representing a field effect transistor is abbreviated as "MIS" in some cases. Note that a MOSFET (Metal Oxide Semiconductor Field Effect Transistor), that is a field effect transistor having a structure in which a gate insulating film thereof is formed of a $SiO_2$ film, is included in a more specific concept of the above-described MISFET. Further, in the embodiments described below, while $Si_3N_4$ is so-called silicon nitride, it includes an insulating film which is made of nitride of silicon having a similar composition. While $SiO_2$ is so-called silicon oxide, it includes an insulating film which is made of oxide of silicon having a similar composition. Further, in the embodiments described below, the term "wafer" mainly indicates a silicon (Si) monocrystalline wafer but it indicates not only the same but also a silicon on insulator (SOI) wafer, a glass wafer, an insulating film substrate for forming an integrated circuit thereon, or the like. The shape of the wafer includes not only a circular shape or a substantially circular shape but also a square shape, a rectangular shape, and the like.

Further, components having the same function are denoted by the same reference symbols in principle throughout all drawings for describing the embodiments described below, and the repetitive description thereof is omitted. Hereinafter, the embodiments of the present invention will be explained in detail based on the drawings.

The embodiments of the present invention will explain means for solving the first problem, the second problem, and the third problem with using a Si-MISFET-type hydrogen gas sensor as one example of a gas sensor. However, it goes without saying that the present invention can be applied to a gas sensor of other system. Further, the embodiments of the present invention will mainly explain a Si-MISFET-type hydrogen gas sensor which is operated by using two lithium cells each having a voltage of 3 V and a current capacity of 2.6 Ah.

[First Embodiment]

A first embodiment relates to first means for solving the first problem, means for solving the second problem, and means for solving the third problem.

First, the first means for solving the first problem will be explained.

Power consumption reduction of a Si-MISFET-type hydrogen gas sensor can be achieved by reducing a surface area size of a heater region to reduce heat dissipation from the surface of the heater region and using a MEMS structure described below to thermally insulate the thermal diffusion of the heater region. Further, the power consumption reduction can be achieved by a structure for suppressing the heat dissipation from a glass substrate by forming a sensor FET on the glass substrate, and besides, for suppressing the heat dissipation from a mounting lead wire through a pad electrode connected to the heater region by a lead-out wiring by down-sizing a sensor chip itself and mounting the sensor chip so as to interpose a heat insulation material having the same area as that of the sensor chip. One example of forming the MISFET on the glass substrate will be described in a second embodiment later.

A basic concept for solving the first problem according to the first embodiment is as follows.

(1) When the whole sensor chip is heated to 100 to 150° C., thermal efficiency is poor and thermal capacity is too large. Therefore, thermal capacity of an intrinsic FET region is suppressed to be 1/100 times a conventional one or less, so that a temperature increase rate is suppressed to be several tens of milliseconds or shorter even in lower power consumption.

(2) A structure in which heater wirings are inserted in spaces between a source electrode and a gate electrode and between a drain electrode and the gate electrode is adopted in order to reduce thermal discharge from the surface of the heater region into the atmosphere gas, so that the surface area of the heater region is made small such as 300 μm×300 μm or smaller.

(3) A thermal resistance of the lead-out wiring from the intrinsic FET region to the pad electrode is largely increased by only slightly increasing a parasitic resistance of the sensor FET.

(4) In order to prevent thermal discharge from the mounting lead wire, the number of mounting lead wires is set to four, a diameter of the mounting lead wire is set to 8 to 25 μm, and a length thereof is set to about 3 to 12 mm.

(5) In order to prevent thermal discharge through the heat insulation material which is inserted between the sensor chip and the mounting substrate (stem base), a foamed glass heat insulation material having an extremely low thermal conductivity is used as that.

(6) By the above-described methods of (1) to (5), a hydrogen gas sensor having such low power consumption as about 25 to 0.3 mW is achieved in a cell operation at a voltage of 3 V.

In the case of the Si-MISFET-type hydrogen gas sensor, a portion which has to be maintained at a predetermined temperature is only a portion of a catalytic metal gate for controlling a channel of the sensor FET. If temperature characteristics of a resistance of the heater wiring are taken, a temperature of the sensor chip can be measured, so that the resistance value of the heater wiring can be used as a thermometer.

Therefore, since a PN-junction diode for measuring the chip temperature is not always required inside the sensor chip, the PN-junction diode is removed, so that the area of the sensor chip can be reduced. By configuring only the sensor FET into a chip, the area of the sensor chip can be reduced, so that only the catalytic metal gate for the sensor FET can be heated, and therefore, an area of a heat source (heater wiring) can be reduced. In this manner, the power reduction can be achieved.

Further, since the number of mounting lead wires can be reduced to four, thermal discharge from the mounting lead wires can be prevented. Since it is only required to maintain the temperature of the catalytic metal gate of the sensor FET at a predetermined temperature in a range of 100 to 150° C., the temperature can be lower than an operation temperature of a typical hydrogen gas sensor which is 400° C.

In consideration of these matters, in the first embodiment, first, an SOI substrate is adopted, a Si substrate for a portion of a sensor FET region of the SOI substrate is bored until the bore reaches an embedded insulation layer (as a MEMS region), and a fold-shaped heater wiring is arranged in spaces between a source electrode and a catalytic metal gate and between a drain electrode and the catalytic metal gate (as a heater region). In this manner, the heater region is smaller than that of a heating structure of other heater arrangement for heating the whole sensor FET region, and therefore, the thermal discharge from the surface of the heater region into the atmosphere gas can be reduced, and besides, the manufacturing process can be simplified by arranging the catalytic metal gate in the heater region.

Hereinafter, a region including the catalytic metal gate for the sensor FET, the source electrode, the drain electrode, and the heater region is referred to as "intrinsic FET region".

Further, a structure (thermally-insulated/heat insulation structure) in which heat of the heater region heated by the heater wiring is not circumferentially released is achieved by adopting a structure in which a region where the intrinsic FET region does not overlap with the MEMS region is formed so that thermal resistance of an insulating thin film for covering this region is increased. Further, the sensor chip is arranged on a heat insulation material having a high thermal resistance, a lead-out wiring is arranged so that a thermal resistance of the lead-out wiring extending to the mounting lead wire does not increase an effect on electric resistance to the sensor FET or the heater wiring, a thermal resistance of the mounting lead wire is increased, so that a structure for insulating thermal diffusion from the heater region to the mounting substrate (stem base) is formed. In this manner, a sensor having such low power consumption as 25 to 0.3 mW is achieved.

Further, in order to further increase the thermal resistance of the insulating thin film for covering the formed region where the intrinsic FET region does not overlap with the MEMS region, some through-holes are formed in the insulating thin film. In this manner, further power consumption reduction is achieved.

Note that, if the MEMS region is too large, a mechanical strength of the MEMS region is weakened, which results in reduction of reliability for a long period. Accordingly, degradation of the mechanical strength of the MEMS region can be prevented by a reinforced region in which the insulating thin film remains in the region where the intrinsic FET region does not overlap with the MEMS region, and besides, by connecting the intrinsic FET region to an outside of the MEMS region by using the lead-out wiring of the heater wiring and the lead-out wirings of the source electrode, drain electrode, and the catalytic metal gate for the sensor FET.

Further, the structure (thermally-insulated/heat insulation structure) in which the heat of the heater region is not circumferentially released is achieved by making a thermal resistance of the region (hereinafter, referred to as "bridge region") where the intrinsic FET region is connected to the outside of the MEMS region by using these lead-out wirings to be equal to or lower than a thermal resistance of the insulating thin film for covering the region where the intrinsic FET region does not overlap with the MEMS region.

In the first embodiment, the shortest distance between the intrinsic FET region and the MEMS region is formed 1 to 20 times the sum of the widths of all the bridge regions and the widths of all the reinforced regions.

Hereinafter, a configuration condition and an operation condition of the sensor chip for achieving the first means for solving the first problem will be summarized.

It is assumed that a thermal resistance of thermal flow from the sensor chip via the heat insulation material to the mounting substrate is represented as "$R_D$", that total thermal resistance of a thermal resistance from the heater region to a plurality of pad electrodes which are formed on the sensor chip connected to the mounting lead wires and thermal resistances of a plurality of mounting lead wires is represented as a thermal resistance "$R_L$", and that a thermal resistance due to the thermal discharge from the surface of the heater region into the atmosphere gas is represented as "$R_A$". And, when it is assumed that the radius of the circle having the same area as the surface area of the heater region is represented as "$r_A$" and that a thermal conductivity of air at the temperature of the heater region is represented as "$\lambda$", the thermal resistance $R_A$ can be approximated by using a thermal resistance "$1/(4\pi\lambda \cdot r_A)$" from a circular heating body having the radius of $r_A$.

Therefore, when it is assumed that a temperature difference between the set temperature Ts of the heater region and the environmentally-assumed lowest temperature Temin in the installation of the hydrogen gas sensor is represented as "$\Delta$Tmax(=Ts−Temin)" and that the heater maximum power supplied to the heater wiring which is determined by the electric resistance R(Ts) of the heater wiring at the set temperature Ts and the used power source voltage Vdd is represented as "Powmax", if the heater maximum power Powmax is 25 mW or less, a required condition is to set the thermal resistances $R_D$ and $R_L$ and the surface area of the heater region so as to satisfy the following Expression (1).

$$\text{Powmax}/\Delta\text{Tmax} > 1/R_D + 1/R_L + 4\pi\lambda \cdot r_A \quad \text{Expression (1)}$$

The environmentally-assumed lowest temperature Temin in the installation of the hydrogen gas sensor is about −65° C., and the set temperature Ts of the heater region can be considered to be substantially the operation temperature of 115° C. in the case of the Si-MISFET-type hydrogen gas sensor in operation at the temperature of 115° C. which is a standard chip temperature. Therefore, in this case, the temperature difference $\Delta$Tmax becomes 180° C. (=Ts−Temin).

Further, the thermal capacity of the heater region can be reduced by three digits or more by adopting such an MEMS structure, and therefore, the arrival time t0 for an increase rate or a decrease rate of a temperature can be reduced. Therefore, the structure is suitable for the intermittent operation of the heater wiring, and the duty ratio ($\tau_1/(\tau_1+\tau_2)$) can be reduced down to, for example, about 1/14 as described below, and therefore, the power consumption can be effectively reduced by one digit or more as compared with that in the continuous operation. Practically, in the case of the hydrogen gas, the duty ratio is in a range of 1/14 to 1.0.

The heater maximum power Powmax is determined by the power source voltage Vdd (which is 3 V in the case of the hydrogen gas sensor operated by two lithium cells having a current capacity of 2.6 Ah) and the electric resistance R(Ts) of the heater wiring at the set temperature Ts. Practically, when the electric resistance R(Ts) of the heater wiring is set to be too large, the heater maximum power Powmax becomes too small. When the temperature difference ΔT is set to be too large by increasing the operation temperature of the hydrogen gas sensor, there is no realistic combination of the thermal resistances $R_D$ and $R_L$ and the surface area of the heater region which satisfies the Expression (1). Therefore, in the case of the hydrogen gas sensor, as reducing the heater maximum power Powmax, it becomes significantly difficult to achieve the structure having the temperature difference ΔT=150° C. and the operation chip temperature of 115° C.

On the other hand, as increasing the heater power Pow, it is necessarily easier to obtain the realistic combination of the thermal resistances $R_D$ and $R_L$ and the surface area of the heater region which satisfies the Expression (1). However, in the case of the hydrogen gas sensor, the response speed is required within 30 seconds, and therefore, the duty ratio is limited. Therefore, the heater power Pow cannot be increased needlessly, and an upper limit of the heater maximum power Powmax becomes 25 mW as described below. In a case of a Si-MISFET-type hydrogen gas sensor with a Pt—Ti—O gate according to the first embodiment, a response speed close to one second is shown in a region of a hydrogen concentration from 1000 ppm to several percentages, and therefore, a lower limit of the duty ratio can be down to about 1/14. Since an upper limit of the power consumption in the continuous operation which can guarantee the operation for one year by using two lithium cells is 1.78 mW, the upper limit of the power consumption which allows the operation for one year by two lithium cells is about 25 mW from a relationship of "25 mw×1/14≅1.78 mW". Therefore, the maximum power consumption which can achieve both of the cell capacity and the safety of the hydrogen gas detection is about 25 mW.

In an actual structure, there is a thermal resistance $R_M$ of thermal flow flowing in the bridge region for connecting the intrinsic FET region and the outside of the MEMS region. As decreasing the thermal resistance $R_M$, an effective heater region is increased, so that the thermal resistance of $1/(4\pi\lambda \cdot r_A)$ is decreased, which results in unsatisfaction of the Expression (1). That is, even if power is supplied to the heater wiring, the chip temperature does not reach the set temperature. However, if the thermal resistance $R_M$ is set so that a temperature difference between the intrinsic FET region and an edge of the MEMS region or the pad electrode is about 50% of the temperature difference ΔTmax or higher, thermal diffusion from the heater region to a surrounding thin film or the substrate can be prevented.

Since a degree of freedom of a configuration to the thermal resistances $R_D$, $R_L$, and $r_A$ is high, the hydrogen gas sensor which satisfies the Expression (1) can be achieved in the region of 25 to 0.3 mW.

Incidentally, in order to reduce the power consumption with fixing the temperature of the catalytic metal gate used for the Si-MISFET-type hydrogen gas sensor at, for example, 115° C., it is required to reduce a cross-sectional area of the heater wiring to increase the heater resistance. However, when a density of a current flowing in the heater wiring is too high, a problem such as disconnection arises for the reliability, and therefore, the cross-sectional area of the heater wiring cannot be reduced needlessly. Therefore, instead of a heater wiring made of Al or Au having a low resistivity, WSi, W, polysilicon (polycrystalline silicon), or others having a high resistivity is used. In this manner, the cross-sectional area of the heater wiring can be maintained to such an extent that the problem of the density of the current described above can be avoided so that a length of the heater wiring can be further reduced, and, as a result, the surface area of the heater region is reduced, which results in further reduction in the power consumption.

In the first embodiment, such a case that an n-channel-type MISFET is applied to the sensor FET will be explained. While the catalytic metal gate is used as the gate for the sensor FET, the first embodiment exemplifies a gate having a Pt—Ti—O structure formed by sequentially forming Ti (having a thickness of 5 nm) and Pt (having a thickness of 15 nm) on a gate insulation film by an electron beam deposition method and a lift-off method, and then, performing an air annealing treatment at a temperature of 400° C. for 2 hours.

The gate having the Pt—Ti—O structure according to the first embodiment will be explained below.

The present inventor has found that a hydrogen gas sensor having high hydrogen gas sensitivity can be obtained by applying a heat treatment under air to a Si-MISFET having the gate obtained by stacking a Ti film and a Pt film. The thickness of the Pt film is, for example, 15 nm, the thickness of the Ti film is, for example, 15 nm, the temperature of the heat treatment is, for example, 400° C., and the time for the heat treatment is, for example, 2 hours. An effect obtained by this heat treatment can be understood as follows. That is, the application of the heat treatment to the above-described Ti/Pt stacked film generates a process in which Ti atoms travel along a Pt crystal grain boundary and in a vicinity thereof to reach a surface of the Pt film and a process in which O atoms travel along the Pt crystal grain boundary and in the vicinity thereof to enter into the Ti film. Therefore, the Ti film is converted into a TiO layer (a layer to which high-concentration oxygen is doped and amorphous Ti, amorphous TiO, or fine crystal TiO are mixed), and fine crystal grains having Pt (111) orientation are embedded into the $TiO_x$ layer during this process. An embedding depth is different depending on individual fine crystal grains having Pt (111) orientation, and therefore, surface asperity occurs on an interface between the Pt film and the $TiO_x$ layer. On the other hand, in the grain boundary region between the Pt fine crystal grains through which the Ti atoms and the O atoms have passed, a structure having a Pt—Ti—O region to which high-concentration oxygen is doped and which is made of Pt—Ti is formed. Hereinafter, a catalytic metal gate having such a structure that the Pt—Ti—O region is arranged is referred to as "Pt—Ti—O gate", and a MISFET having the Pt—Ti—O gate is referred to as "Pt—Ti—O gate Si-MISFET".

Next, a structure of the Pt—Ti—O gate Si-MISFET-type hydrogen gas sensor according to the first embodiment to which the structure condition and the operation condition of the sensor chip for achieving the above-described first means for solving the first problem will be explained in detail.

Figure 1:
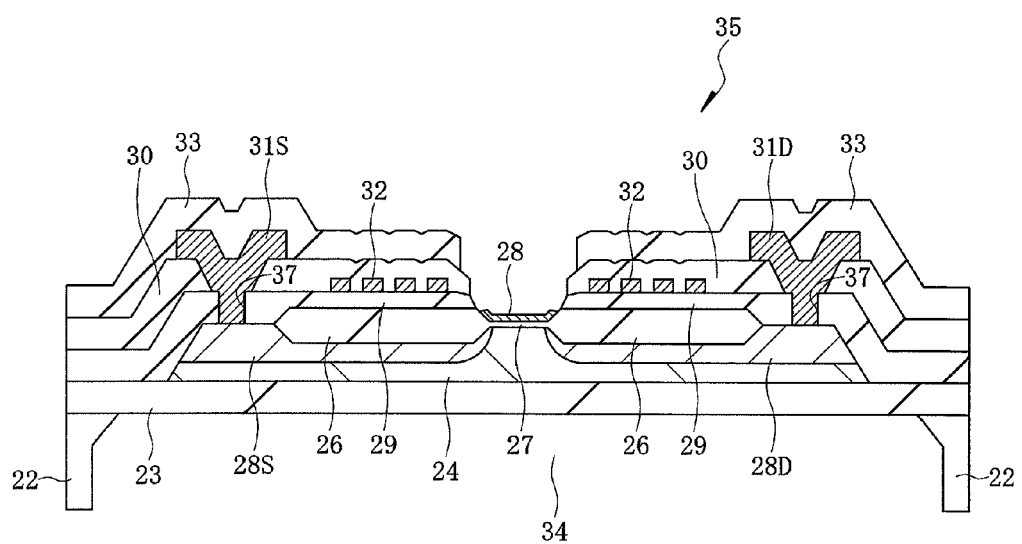
FIG. 1 is a cross-sectional view of a principal part of a sensor MISFET according to a first embodiment of the present invention.
Figure 2:
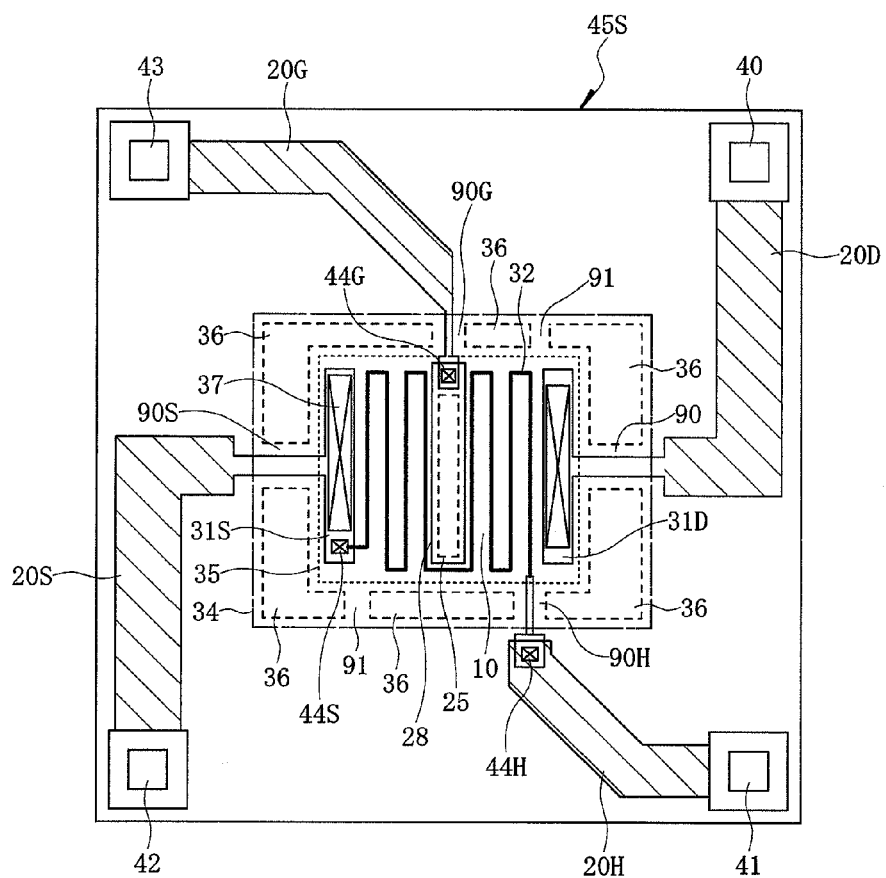
FIG. 2 is a plan view of a principal part of a sensor chip according to the first embodiment of the present invention.

With reference to FIGS. 1 to 5B, the first means for solving the first problem according to the first embodiment will be explained. FIGS. 1 and 2 are a cross-sectional view of a principal part of the sensor FET and a plan view of a principal part of the sensor chip, respectively, FIGS. 3A and 3B are a plan view of a partially-enlarged principal part of a bridge region formed in a MEMS region and a cross-sectional view of the principal part taken along line A-A' in FIG. 3A, respectively, FIGS. 4A, 4B, and 4C are a cross-sectional schematic view of a hydrogen gas sensor on which the sensor chip is mounted, a rear-surface schematic view of a stem base, and a front-surface schematic view of the stem base, respectively, and FIGS. 5A and 5B are a graph diagram for explaining power consumption characteristics (Expression (1)) and a graph diagram for explaining power consumption characteristics of a heater of the hydrogen gas sensor, respectively.

First, the sensor chip will be explained with reference to FIGS. 1, 2, and 3A and 3B. FIG. 1 illustrates a principal part of a sensor FET, a heater wiring, a lead-out wiring, and others formed on an SOI substrate. FIG. 2 illustrates the principal part of the sensor chip, the heater wiring, the lead-out wiring, a pad electrode, and others formed on the SOI substrate.

As illustrated in FIG. 1, an embedded insulation layer ($SiO_2$ layer) 23, a channel layer (Si layer) 24, $n^+$-Si layers 28S and 28D, a gate insulation layer ($SiO_2$ film) 27, a gate electrode made of Pt—Ti—O (Pt—Ti—O gate, catalytic metal gate) 28, a source electrode 31S, a drain electrode 31D, and the like are formed on an Si substrate 22. A gate length of the Pt—Ti—O gate 28 is, for example, 5 μm, a gate width thereof is, for example, 20 μm. A thickness of the channel layer 24 is, for example, 0.1 to 5 μm, and a typical thickness thereof can be exemplified as 0.2 μm. A thickness of the embedded insulation layer 23 is in a range of, for example, 0.1 to 5 μm, and a typical thickness thereof can be exemplified as 3 μm. A thickness of the Si substrate 22 is, for example, 200 to 750 μm, and a typical thickness thereof can be exemplified as 500 μm.

Further, the thermal conductivity λ of the Si crystal is reduced by doping. Therefore, if the heat insulation is desired as the first embodiment, a p-type Si substrate obtained by doping high-concentration p-type impurities into the Si substrate 22 is used. In this manner, the thermal conductivity λ is reduced down to about ⅓ of that of the Si crystal to which the impurities are not doped, and therefore, the heat insulation property is improved. In the first embodiment, a p-type Si substrate obtained by adding B (boron) into the Si substrate 22 is used. However, a high-concentration SOI substrate can also be used.

In the first embodiment, after the $n^+$-Si layers 28S and 28D are formed by an ion-implantation method, and are subjected to thermal annealing treatment for activation, so that a local oxidation film ($SiO_2$ film) 26 is formed by promotional oxidation in this thermal annealing treatment. After the $n^+$-Si layers 28S and 28D are formed below the local oxidation film 26, the $n^+$-Si layers 28S and 28D and the channel layer 24 in a region are selectively removed, the region being except for an intrinsic FET region 35 where the source electrode 31S, the drain electrode 31D, and the principal part of the Pt—Ti—O gate 28 for the sensor FET are formed. An aim of this is to efficiently thermally insulate the intrinsic FET region 35 because, when the area of the channel layer 24 is large, heat quantity heated by the heater wiring 32 and flown into the intrinsic FET region 35 is easily circumferentially released since the thermal conductivity of the channel layer 24 is about two digits higher than that of $SiO_2$. For example, the thermal conductivity λ of the undoped monocrystalline Si substrate is 148 W/(m·° C.), the thermal conductivity λ of $SiO_2$ is 1.4 W/(m·° C.), and the thermal conductivity λ of $Si_3N_4$ is 25 W/(m·° C.). The thermal conductivity λ of $Si_3N_4$ is changed by a manufacturing condition in a range of about 0.9 to 40 W/(m·° C.). However, the thermal conductivity of the $Si_3N_4$ film can be designed by changing the film thickness thereof.

As illustrated in FIGS. 1 and 2, a gate region 25 has a rectangular shape surrounded by the local oxidation film 26 and a PSG (phosphorus-doped glass) protective film 29, and the channel layer 24 is formed in the gate region 25 so as to interpose a gate insulation film 27. The Pt—Ti—O gate 28 is formed by sequentially forming a Ti film (having a thickness of, for example, 5 nm) and a Pt film (having a thickness of, for example, 15 nm) by an electron beam deposition method so as to mount on an edge of the local oxidation film 26 by a lift-off method. At this time, an air annealing treatment is performed at a temperature of 400° C. for 2 hours. A width of the Pt—Ti—O gate 28 is designed so as to be larger than the gate length by 3 μm such as 8 μm.

A PSG protective film 29 for gate protection is formed on the $n^+$-Si layers 28S and 28D and the local oxidation film 26 except for the gate region 25 by a thermal CVD (Chemical Vapor Deposition) method. Further, on the PSG protective film 29, a heater wiring 32 made of WSi is formed. A thickness of the PSG protective film 29 is, for example, 300 nm. A thickness of the heater wiring 32 is, for example, 300 nm, a wire width thereof is, for example, 1 μm, and a resistivity thereof at a temperature of 115° C. is, for example, 300 μΩm. For example, the heater wiring 32 is formed between the Pt—Ti—O gate 28 and the source electrode 31S in an accordion-fold shape formed of four lines having a line interval of 1 μm therebetween based on a length unit of 30 μm, and the heater wiring 32 is similarly formed between the Pt—Ti—O gate 28 and the drain electrode 31D. In this case, a total length of the heater wiring 32 is about 250 μm. A resistance of the heater wiring 32 is, for example, 1.5 kΩ at the temperature of 115° C.

On the heater wiring 32, a PSG protective film 30 is formed by a thermal CVD method. A thickness of the PSG protective film 30 is, for example, 300 nm. Further, in the PSG protective film 30, contact holes (having a size of, for example, 3 μm-square) 44H and 44S for connection to the heater wiring 32 and a contact hole (having a size of, for example, 3 μm-square) 44G for connection to the Pt—Ti—O gate 28 are formed. In the PSG protective films 29 and 30, contact holes 37 for connection to the $n^+$-Si layers 28S and 28D are formed.

Further, a lead-out wiring 20H connected to one end of the heater wiring 32 via the contact hole 44H is formed, a lead-out wiring 20S connected to the other end of the heater wiring 32 via the contact hole 44S is formed, and a lead-out wiring 20G connected to the Pt—Ti—O gate 28 via the contact hole 44G is formed. And, a source electrode 31S connected to the $n^+$-Si layer 28S and a lead-out wiring 20S in the same layer as the source electrode 31S are formed, and a drain electrode 31D connected to the $n^+$-Si layer 28D and the a lead-out wiring 20D in the same layer as the drain electrode 31D are formed. The lead-out wirings 20S, 20D, 20G, and 20H are made of Al formed by, for example, a sputtering method, and each thicknesses thereof is, for example, 500 nm. The lead-out wiring 20S is electrically connected to the other end of the heater wiring 32 via the contact hole 44S and to the source electrode 31S via the contact hole 37. The lead-out wirings 20S, 20D, 20G and 20H are connected to pad electrodes 40, 41, 42 and 43 formed in periphery of a sensor chip 45S, respectively.

Further, a final protective film 33 is formed on the lead-out wirings 20S, 20D, 20G and 20H, the source electrode 31S, the drain electrode 31D, and others. This final protective film 33 is formed of, for example, a stacked film whose lower layer is a PSG film and whose upper layer is a $Si_3N_4$ film. The PSG film of the lower layer is formed by, for example, a thermal CVD method, and a thickness thereof is, for example, 200 nm. The $Si_3N_4$ film of the upper layer is formed by, for example, a low-temperature plasma CVD method, and a thickness thereof is, for example, 1 μm.

The Si substrate 22 is bored so that the boring reaches the embedded insulation layer 23 in a MEMS region 34 (a planar dimension is, for example, 200 μm×200 μm) where a heater region 10 (a planar dimension is, for example, 30 μm×24 μm) and the intrinsic FET region 35 (a planar dimension is, for example, 44μ×44 μm) are arranged, the heat region where the principal part of the heater wiring 32 is formed and the intrinsic FET region where the source electrode 31S, the drain electrode 31D, and the principal part of the Pt—Ti—O gate 28 for the sensor FET are formed. This structure is formed by a combination method of anisotropic dry etching and wet etching with using KOH solution. A threshold voltage of the sensor FET is designed to, for example, 1 V. The threshold voltage of the sensor FET is defined by a gate voltage Vg which provides a source-drain current Ids=5 µA in a range of a drain voltage Vds=1.5 to 3 V.

Next, a structure in which the heat from the heater region 10 according to the first embodiment is adiabatically confined in the MEMS region 34 will be explained.

In the case of the hydrogen gas sensor, operation at a temperature of 100 to 150° C. is desired. When the set temperature (normal operation temperature) Ts of the heater region 10 is set to 115° C. in consideration of margin, it is required to increase a calorific value (heater power Pow) generated by the heating of the hydrogen gas sensor as decreasing the environmental temperature Te at which the hydrogen gas sensor is installed. The channel layer 24 and the $n^+$-Si layers 28S and 28D made of Si which is excellent in the thermal conductivity exist below the heater wiring 32 of the intrinsic FET region 35, so that an effect of improving uniformity of the temperature of the heat generation from the heater wiring 32 can be obtained.

In the first embodiment, the heater regions 10 are arranged so as to interpose the Pt—Ti—O gate 28 therebetween, and the arrangement is extremely small, and therefore, it can be considered that the temperature of the heater region 10 and the temperature of the Pt—Ti—O gate 28 are almost equal to each other. In consideration of the thermal diffusion from the heater region 10 to the environment where the hydrogen gas sensor is installed, when it is assumed that a thermal resistance between them is represented as "Rth", a temperature difference ΔT(=T−Te) determined by the temperature T of the heater region with the environmental temperature Te and the heater power Pow is expressed as the following Expression (2).

$$\Delta T = Rth \times Pow \qquad \text{Expression (2)}$$

When −35° is assumed for the environmental temperature Te as the lowest temperature of the environment in the average installation, the temperature difference ΔT is 150° C. at the operation temperature of 115° C. In the first embodiment, the heater resistance at the operation temperature of 115° C. is 1.5 kΩ. In consideration of the cell operation at 3 V, the heater maximum power Powmax is 6 mW and the temperature difference ΔTmax is 180° C.

Generally, the largest temperature difference ΔT is about 150° C., and the heater power Pow is 5 mW in the case of the continuous current conduction. In consideration of heater control for the intermittent operation, the continuous operation for one year or longer can be achieved by using two lithium cells. The thermal capacity of the MEMS region 34 becomes about 1/10,000 of the thermal capacity (about 270 µW second/° C.) of the Si-MISFET-type hydrogen gas sensor having the 2-mm-square sensor chip (the thickness of the Si substrate is 0.4 mm) described above in, for example, the Non-Patent Document 2, and, when the chip temperature is increased in the supplied power of 5 mW from the environmental temperature Te to the 150° C., the arrival time t0 can be extremely shortened to about 2.0 ms. Therefore, by the intermittent operation that the heater wiring 32 is turned on (is heated) for 6 seconds and the heater wiring 32 is turned off (is stopped to be heated) for 24 seconds, the duty ratio can be taken as 1/5, so that the effective power consumption of the hydrogen gas sensor can be reduced down to 1 mW without reducing the reliability of the detection performance of the hydrogen gas sensor. In this manner, the operation for about one year can be achieved by using two lithium cells having a voltage of 3 V.

Further, each of the lead-out wirings 20S, 20D, 20G and 20H is formed of an Al film, and a thermal conductivity λ of the Al film is 237 W/(m·° C.) as metal. However, when the film is thin, it is reduced down to 180 W/(m·° C.). A thermal conductivity of the WSi film is about 90 W/(m·° C.), and both the films become main thermal flow channels from the heater region 10. Therefore, such devisal as explained below is required.

In the first embodiment, in order to thermally insulate the heat generation in the heater region 10 in a better manner, a structure in which the sensor chip 45 is occupied by air which has extremely-excellent heat insulation characteristics is adopted, the structure being achieved by partially removing the PSG protective films 29 and 30 and the protective film 33 in the region where the intrinsic FET region 35 does not overlap with the MEMS region 34, and besides, arranging the plurality of through-holes 36 penetrating through the embedded insulation layer 23. A relative distance between the intrinsic FET region 35 and the MEMS region 34 is 78 µm, air exists below the MEMS region 34, and a thermal conductivity λ of the air at the temperature of 115° C. is extremely low as 0.03227 W/(m·° C.), and therefore, the thermal insulation characteristics of this structure are excellent. However, if the through-holes 36 are formed too large, the mechanical strength of the MEMS region 34 is degraded. Meanwhile, although the protective film 33 formed of the $Si_3N_4$ film is required to protect the heater wiring 32 and the lead-out wirings 20S, 20D, 20G and 20H, it has the thermal conductivity which is about one digit higher than that of $SiO_2$, and therefore, when the power consumption is lowered, the heat insulation characteristics of the bridge region where the lead-out wirings 20S, 20D, 20G and 20H are formed are not ignorable.

Figure 3A:
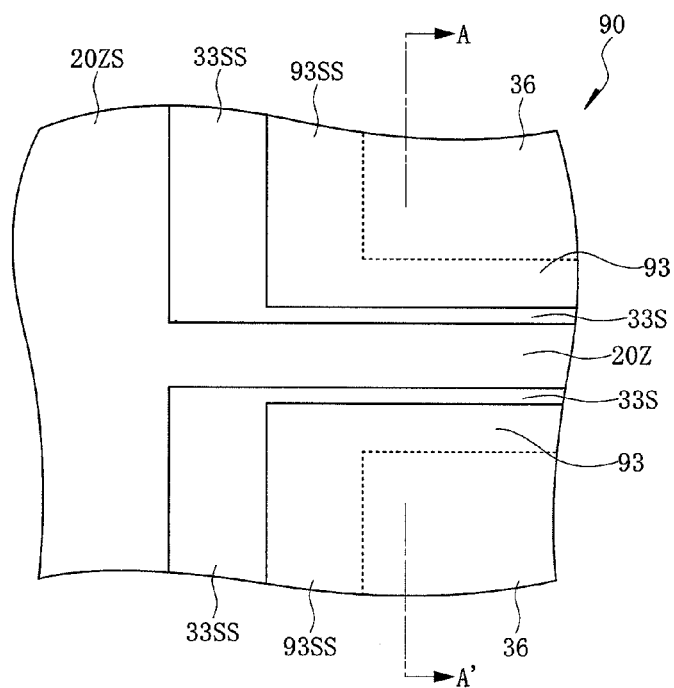
FIGS. 3A and 3B are a plan view of a partially-enlarged principal part of a bridge region formed in an MEMS region according to the first embodiment of the present invention and a cross-sectional view of a principal part taken along line A-A' in FIG. 3A, respectively.
Figure 3B:
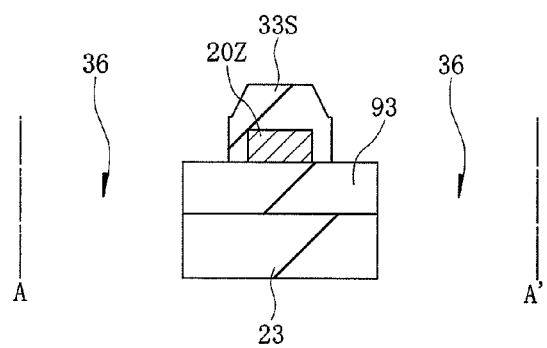

In consideration of these points, a method of achieving the heat insulation will be explained with reference to a plan view and a cross-sectional view illustrated in FIGS. 3A and 3B, respectively. FIG. 3A is an enlarged view of a peripheral portion of the bridge region 90 in FIG. 2. A length of the bridge region 90 is, for example, 78 µm. A wire width of a lead-out wiring 20Z of the bridge region 90 is, for example, 2 µm, a wire width of a protective film 33S is, for example, 3 µm, a wire width of a stacked film 93 of the PSG protective films 29 and 30 is, for example, 6 µm. Further, in a peripheral portion of the intrinsic FET region 35, a relative distance between a lead-out wiring 20ZS and a protective film 33SS is, for example, 3 µm, and a relative distance between the protective film 33S and the stacked film 93SS of the PSG protective films 29 and 30 is, for example, 3 µm. This structure is the same even in a bridge region 90G of the lead-out wiring 20G connected to the Pt—Ti—O gate 28, a bridge region 90H of the lead-out wiring 20H connected to one end of the heater wiring 32, and a bridge region 90S connected to the lead-out wiring 20S connected to the source electrode 31S and the other end of the heating wire 32. In order to reinforce the MEMS region 34, a width of a reinforced region 91 where the stacked layer of the PSG protective films 29 and 30 is formed is also, for example, 6 µm. When a distance between an edge of the MEMS region where the through-hole 36 is formed and an edge of the FET region is defined as a length of the bridge region 90, it is 78 µm in the first embodiment which is the closest distance between the edge of the intrinsic FET region and the edge of the MEMS region, and therefore, it is about 2.2 times the sum of the widths of all the bridge regions 90, 90S, 90G and 90H and the widths of all the reinforced regions 91 which is 36 μm (6 μm×6 lines), and it is usually formed 1 to 20 times the sum.

In the bridge regions 90, 90S, 90G, and 90H, when it is assumed that the thickness of the $Si_3N_4$ film forming the protective film 33 is, for example, 1 μm and that the PSG is $SiO_2$, the thickness of the protective films 29 and 30 is 3.8 μm in conversion to $SiO_2$. In consideration of 1.4 W/(m·° C.) as the thermal conductivity of $SiO_2$, 25 W/(m·° C.) as the thermal conductivity of $Si_3N_4$, 180 W/(m·° C.) as the thermal conductivity of the Al thin film, and 90 W/(m·° C.) as the thermal conductivity of the WSi thin film, the thermal resistance of the bridge region 90 is $9.1\times10^{4}$° C./W in three bridge portions related to the lead-out wirings 20S, 20D, and 20G, it is $39.65\times10^{4}$° C./W in one bridge portion related to the lead-out wiring 20H, and it is $12.22\times10^{4}$° C./W in two bridge portions related to the reinforced regions 91. These three thermal resistances are connected in parallel, so that a thermal resistance $R_M$ from the heater region 10 to the MEMS region becomes $4.61\times10^{4}$° C./W. In this case, thermal conduction due to the through-holes 36 is ignorable.

Further, it is estimated from the thermal conductivity of air which is 0.03227 W/(m·° C.) that a thermal resistance of a heat insulation material (whose reference symbol is 50 in FIG. 4A described later) from the MEMS region 34 through the bored region in the MEMS region 34 to the front surface is $7.75\times10^{5}$ ° C/W, the heat insulation material being sandwiched between the sensor chip and the stem base. However, it is one or more digit higher than the thermal resistance $R_M$ of the heater region 10, and therefore, is ignorable. That is, when the power of 5 mW is supplied to the heater region 10, the temperature difference between the bridge region and the heater region 10 becomes 230.5° C.(=$4.61\times10^{4}$° C/W×5 mW), and therefore, a sufficient heat-insulation effect can be expected.

On the other hand, since the thermal conductivity of the $Si_3N_4$ film forming the protective film 33 is one or more digit larger than that of $SiO_2$, the $Si_3N_4$ film is removed while remaining on the region where the intrinsic FET region 35 and the lead-out wirings 20S, 20D, 20G, and 20H are formed and the peripheral region of the above-described bridge region. A portion of the lead-out wirings 20S, 20D, 20G, and 20H illustrated by hatching maintains the small influence of the electric resistances of the lead-out wirings on the sensor FET, so that the thermal resistance is increased. Therefore, for example, it is designed by taking a zigzag structure (which is omitted in FIG. 2) or others having a width thereof is, for example, 10 μm, and a length thereof is, for example, 700 μm. At this time, the thermal resistance of all the lead-out wirings is about $1.94\times10^{5}$° C./W. However, except in the MEMS region 34, the thermal conduction occurs through the Si substrate 22 having the high thermal conductivity, and therefore, contribution to the thermal resistance $R_L$ is small in the MEMS system.

Next, a structure in which the heat from the heater region 10 according to the first embodiment is thermally insulated from the mounting substrate by the heat insulation material of the sensor chip will be explained. FIGS. 4A, 4B, and 4C are views for explaining a basic configuration of a hydrogen gas sensor obtained by mounting the sensor chip according to the first embodiment on a stem including four lead terminals. FIGS. 4A, 4B, and 4C are a cross-sectional view of the hydrogen gas sensor on which the sensor chip is mounted, a bottom-surface view of a stem base when the hydrogen gas sensor is viewed from a rear surface thereof, and a top-surface view of the stem base on which the sensor chip is mounted, respectively. Since the mounting illustrated in the first embodiment is a simple explosion-proof mounting, it is desired that the mounting portion is constructed by using commercialized products.

The mounting illustrated in the first embodiment is swaged from an inside thereof by, for example, using PEEK material (polyether ether ketone material) 57 having a thickness of 3 mm. A Kovar-manufactured cap 56 and a flange 54 of the stem base are welded by a resistance welding method. As a water-proof permeable material 58 used in the hydrogen gas sensor according to first embodiment, a GORE-TEX (Registered Trademark) film is used, the GORE-TEX film being manufactured by composing a stretched film of polytetrafluoroethylene which is a typical fluorine resin with a polyurethane polymer. The water-proof permeable material 58 has a feature that moisture is passed through but water is not passed through (having both of the water-proof property and the permeable property). In the example of the GORE-TEX film, the film contains 14 hundred million fine holes per 1 $cm^2$. As a diameter of an intake hole 60, a range of about 0.5 to 2 mm is used. However, significant change of the hydrogen response has not been found. Although performances in ranges of 1 to 3 μm and 0.3 to 1 mm for the hole diameter and a thickness of the water-proof permeable material 58 have been compared, respectively, significant change has not been observed.

As the heat insulation material 50 formed on the 4-pin Kovar-manufactured stem base 51 (an inner diameter of the base is 4.22 φ), a foamed glass (whose thermal conductivity is 0.061 W/(m·° C.)) is used. This is worked in, for example, a rectangular parallelepiped shape having a planar dimension of 0.6 mm×0.6 mm and a height of 3 mm, and is bonded to the stem base 51. A thickness of the sensor chip 9 is, for example, 500 μm, and a planar dimension of the sensor chip 9 is, for example, 0.55 mm×0.55 mm. A height of a cap 56 is, for example, 12 mm, and a diameter of the intake hole 60 is, for example, 1.5 mm. A hole diameter of the water-proof permeable material 58 is, for example, 1.0 μm, and a thickness thereof is, for example, 0.3 mm. In the stem base 51, four lead terminals 55 penetrating through the stem base 51 and protruding outside the front surface and the rear surface of the stem base 51 are provided. The lead terminals 55 are fixed to the stem base 51 by a glass material 61 provided in an outer circumference of the lead terminals 55. In FIG. 4A, a dimension denoted by a reference symbol 59 is a cap size.

A lead wire (wire bonding) 8 is a gold wire, and a diameter thereof is, for example, 8 to 25 μm, and an overall length thereof is 3 to 12 mm. Typically, for example, a lead wire made of a gold wire having a diameter of 8 μφ and a length of 6 mm is used, and the above-described four pad electrodes 40, 41, 42, and 43 illustrated in FIG. 2 and the four lead terminals 55 are connected by the respective lead wires 8. A total thermal resistance $R_L$ of these four lead wires 8 is, for example, about $9.41\times10^{4}$° C/W. In this case, the thermal resistance does not contain the thermal resistances from the heater region 10 to the pad electrodes 40, 41, 42, and 43, and therefore, it is considered that $9.41\times10^{4}$° C/W is the minimum value of the thermal resistance $R_L$. Further, a thermal resistance $R_D$ of the heat insulation material 50 is $1.36\times10^5$ W/° C.

Since an area of the heater region 10 is, for example, 30 μm×24 μm, a radius $r_A$ of a circle of this area is 15.1 μm, so that "$4\pi\lambda r_A$" is expressed as $0.613\times10^{-5}$° C./W by using the thermal conductivity λ (0.03227 W/ (m·° C.)) of air at the temperature of 115° C.

Next, a physical meaning of the above-described expressions (1) and (2) will be explained with reference to FIG. 5A. FIG. 5A is a graph diagram for explaining a relationship between the heater power Pow supplied to the heater wiring and the temperature difference $\Delta T(=T-Te)$ between the operation temperature T of the hydrogen gas sensor and the environmental temperature Te at which the hydrogen gas sensor is installed. The heater maximum power supplied to the heater wiring and determined by the electric resistance R(Ts) of the heater wiring at the set temperature Ts and the used power source voltage Vdd is represented as "Powmax".

In the case of the first embodiment, Ts=115° C., R(TS)=1.5 kΩ, and Vdd=3V, so that the heater maximum power Powmax is 6 mW. Meanwhile, Temin=−65° C. and Ts=115° C., so that the temperature difference $\Delta Tmax(=Ts-Temin)$ between the set temperature Ts of the heater region and the environmentally-assumed lowest temperature Temin at which the hydrogen gas sensor is installed is 180° C. A relationship between the temperature difference $\Delta T$ and the heater power Pow whose slope is "the thermal resistance $\Delta Tmax/Powmax$" is illustrated by a dotted straight line in FIG. 5A.

A relationship between the temperature difference $\Delta T$ of the hydrogen gas sensor and the heater power Pow according to the first embodiment is illustrated by a solid straight line in FIG. 5A. A thermal resistance Rth is higher than the thermal resistance $\Delta Tmax/Powmax$, and satisfies the following relationship.

$$Rth > \Delta Tmax/Powmax \qquad \text{Expression (3)}$$

In this case, the relationship indicates that the hydrogen gas sensor can be necessarily operated by the power consumption of the heater maximum power Powmax or lower within a range of the temperature difference $\Delta Tmax=180°$ C. at the lowest environmental temperature −65° C. to the temperature difference $\Delta T=45°$ C. at the highest environmental temperature 70° C. as an assumed external environmental temperature. It is found that, in a case of 25° C. (a case of the temperature difference $\Delta T=90°$ C.) which is a normal environmental temperature, the power consumption can be ½ of that in the case of the temperature difference $\Delta Tmax=180°$ C., and only the power consumption of 3 mW is required even in "Rth=$\Delta Tmax/Powmax$" which is the lowest thermal resistance.

That is, when the expression (3) is satisfied, FIG. 5A illustrates that a temperature difference $\Delta T$ within a desired range can be necessarily achieved by the power consumption of the heater maximum power Powmax or lower. A required condition for satisfying the expression (3) is the above-described expression (1), and all elements in a right hand side of the expression (1) are measurable amounts, and elements in a left hand side thereof are amounts determined from an operation specification of the hydrogen gas sensor.

In the case of the operation at the sensor temperature of 115° C. which is the condition used in the first embodiment, the heater power Pow (150) corresponding to the temperature difference $\Delta T=150°$ C. is 5 mW in the first embodiment, the temperature difference $\Delta T$ being determined from the thermal resistance $\Delta Tmax/Powmax$ in the range between the temperature difference $\Delta Tmax=180°$ C. at the lowest environmental temperature of −65° C. and the temperature difference $\Delta T=45°$ C. at the highest environmental temperature of 70° C.

As described above, in the hydrogen gas sensor illustrated in the first embodiment, $1/R_D=0.735\times10^{-5}$ W/° C., $1/R_L=1.063\times10^{-5}$ W/° C., and $4\pi\lambda r_A=0.613\times10^{-5}$ W/° C., and therefore, Powmax/$\Delta Tmax$ in the left hand side of the Expression (1) is $3.333\times10^{-5}$ W/° C., which satisfies the Expression (1).

FIG. 5B illustrates a graph diagram for explaining a relationship between the resistance of the heater wiring and the power consumption in a case that the hydrogen gas sensor mounted in such a manner is operated at the temperature of 115° C. under the environment at the external temperature of −35° C. so that current is carried through the heater wiring. When current of 1.83 mA is carried through, the resistance of the heater wiring is 1.5 kΩ, and a temperature of a gate region is 115° C. A voltage applied to the lead-out wires (the pad electrode 41 and the pad electrode 42) for the heater wiring is about 2.74 V, and a power consumption is 5 mW.

Next, the means for solving the second problem will be explained.

The means for solving the second problem according to the first embodiment will be explained with reference to FIGS. 6A to 7B. FIGS. 6A and 6B are a graph diagram for explaining controllability of a threshold voltage and a graph diagram for explaining time responses of hydrogen response outputs (a graph diagram for explaining time responses of hydrogen response outputs "before and after air annealing treatment at a temperature of 400° C. for 2 hours" and time response of hydrogen gas output "after air annealing treatment at a temperature of 400° C. for 2 hours+hydrogen annealing treatment at a temperature of 115° C. for 10 minutes with 0.1% air-diluted hydrogen), respectively. FIGS. 7A and 7B are a wafer in-plane distribution diagram of a threshold voltage for explaining the wafer in-plane distribution and repeatability of the threshold voltage, and a diagram for explaining a wafer in-plane distribution of the hydrogen response output, respectively. In experiments for obtaining measurement results illustrated in FIGS. 6A and 6B, the threshold voltage Vth is a gate voltage Vg obtained when the hydrogen response is measured, and it is defined that the gate voltage Vg at which the source-drain current Ids shows 10 µA in the source-drain voltage Vds of 1.5 V is the threshold voltage Vth.

In the Pt—Ti—O gate Si-MISFET-type hydrogen gas sensor according to the first embodiment, the improvement of the uniformity and the repeatability of the threshold voltage of the Pt—Ti—O gate Si-MISFET-type hydrogen gas sensor has not been studied yet. In order to expand a design margin of an interface circuit for taking out a hydrogen gas response signal of the sensor MISFET, it is required to reduce a residual response intensity generated after the hydrogen gas irradiation is turned off so as to improve the controllability (the uniformity and the repeatability) of the threshold voltage in the Pt—Ti—O gate Si-MISFET.

For the second problem, the residual response intensity generated after the hydrogen gas irradiation to the Si-MISFET equipped with the gate having the PT-Ti—O structure is stopped, so that the controllability (the uniformity and the repeatability) of the threshold voltage Vth is improved.

That is, when the hydrogen gas irradiation to the Pt—Ti—O gate Si-MISFET is stopped, a residual hydrogen-gas response intensity $\Delta Vgres$ having a very long time constant is frequently generated. This residual hydrogen-gas response intensity $\Delta Vgres$ is undesirable for the hydrogen gas detection, and is desirable to be very smaller than the hydrogen-gas response intensity $\Delta vg$. From the studies made by the present inventor, it has been found that this phenomenon results from a matter that a deep trap level which increases a speed of adsorption of hydrogen atoms but decreases a speed of desorption of the hydrogen atoms is generated in an oxygen-doped Ti layer. Further, it has been found that the residual hydrogen-gas response intensity $\Delta Vgres$ is reduced down to be very small by hydrogen termination for this deep hydrogen trap level, and besides, the controllability (the uniformity and the repeatability) of the threshold voltage Vth can be significantly improved. That is, by this hydrogen termination process, hydrogen molecules are dissociated on a surface of the Pt—Ti—O gate, and the hydrogen termination for the deep hydrogen trap in the above-described oxygen-doped Ti layer is performed through a diffusion step (hydrogen diffusion through the vicinity of Pt grain boundaries), so that the threshold voltage Vth can be stabilized, and besides, the uniformity and the repeatability of the hydrogen-gas response intensity ΔVg can be significantly improved. This hydrogen termination process has a feature that the process advances in a direction of the reduction in the threshold voltage Vth (a reverse direction of the threshold voltage Vth in the conventional hydrogen gas irradiation).

The present inventor has found that, when Pd is formed on the gate insulation film by a sputtering method, sputter damage occurs in the gate insulation film, and the threshold voltage Vth fluctuates in a range of about 2 V. And, it is considered that the effect obtained by the hydrogen process in the above-described Non-Patent Document 5 also results from the sputter damage. The Non-Patent Document 5 is different in that positive and negative of the result values are turned into a reverse direction of the results of the change of the threshold voltage Vth of the PT-Ti—O gate Si-MISFET according to the first embodiment. Further, this Non-Patent Document 2 is for not the improvement of the hydrogen gas response intensity but the improvement of the response speed (improvement from 50 hours to 55 seconds), and is different in that the response speed of 55 seconds for the 1% air-diluted hydrogen gas is provided even after the hydrogen annealing treatment, which is extremely slower than the response speed of about 1 second of the PT-Ti—O gate Si-MISFET-type hydrogen gas sensor according to the first embodiment under the same condition. In consideration of these two different points, it is considered that they are different in the effect of the hydrogen process which is different in a mechanism thereof.

Next, a method of improving the uniformity and the repeatability of the threshold voltage Vth of the sensor FET which is the second problem according to the first embodiment, and an effect obtained by the method will be specifically explained. Note that, here, the uniformity of the threshold voltage Vth means wafer in-plane uniformity caused when a sensor chip is manufactured.

During a step of manufacturing a plurality of sensor chips in a wafer state or after the manufacturing, when the air annealing treatment has been performed to the wafer at the temperature of 400° C. for 2 hours, 0.4 V has remained in both of the responses for the 0.1% air-diluted hydrogen gas as a very long residual hydrogen gas response intensity ΔVgres after the hydrogen gas irradiation is stopped, and variation in the threshold voltage Vth among wafers has been large, which has been about ±0.3 V even in the wafer in-plane distribution.

Accordingly, the present inventor has made the following experiment. Five chips have been taken out from 5 points (upper, middle, lower, left, and right points) inside a 5-inch wafer whose sample number is #4, one chip has been taken out from one point inside a wafer whose sample number is #11, these chips have been subjected to the air annealing treatment at the temperature of 400° C. for 2 hours, and they have been left until their temperature return to a room temperature. And then, the sensor chips have been heated to a temperature of 115° C., and the 0.1% air-diluted hydrogen gas has been irradiated thereto for 2 minutes (hereinafter, which is referred to as "two-minute hydrogen annealing treatment"). The threshold voltages Vth of the sensor chips have been measured before this two-minute hydrogen annealing treatment, and besides, the threshold voltages Vth thereof have been measured after repeating this two-minute hydrogen annealing treatment.

FIG. 6A illustrates a graph diagram for explaining measurement result of the threshold voltages Vth obtained in the repeat of the two-minute hydrogen annealing treatment. A vertical axis thereof indicates the threshold voltages Vth, and a horizontal axis thereof indicates the number of times of the two-minute hydrogen annealing treatment. For the measurement of data illustrated in FIG. 6A, a sensor FET having a gate length of 20 μm and a gate width of 300 μm is used. The number of times of measurement of 1 in FIG. 6A illustrates the threshold voltages Vth obtained by performing the air annealing treatment at the temperature of 400° C. for 2 hours, leaving the chips until the temperatures thereof return to the room temperature, and then, measuring them before the two-minute hydrogen annealing treatment. From this experiment result, it is found that the threshold voltages converge with a fixed value by repeating the two-minute hydrogen annealing treatment.

Further, the value of the residual hydrogen gas response intensity ΔVgres is reduced down to be a very small value of about 0.05 V so as to be associated with the convergence. Accordingly, in order to reduce the residual hydrogen gas response intensity ΔVgres after the air annealing treatment at the temperature of 400° C. for 2 hours and reduce the variation in the threshold voltages Vth for the sensor FET, a treatment of heating the sensor chips to the temperature of 115° C. and irradiating the 0.1% air-diluted hydrogen gas for 10 minutes (hereinafter, referred to as "normal post hydrogen annealing treatment") is performed.

FIG. 6B illustrates a graph diagram for explaining time response characteristics of the sensor FET for 1000-ppm air-diluted hydrogen in a wafer whose sample number is #24. The characteristics of the sample obtained before the air annealing treatment at the temperature of 400° C. for 2 hours are indicated by a small white circle, the characteristics of the sample obtained after the air annealing treatment at the temperature of 400° C. for 2 hours are indicated by a white square, and the characteristics of the sample obtained by the air annealing treatment at the temperature of 400° C. for 2 hours, and then, performing the treatment of heating the sample to 115° C. and irradiating the 0.1% air-diluted hydrogen gas to the sample for 10 minutes (which is the normal post hydrogen annealing treatment) are indicated by a large white circle. It is found that the value of the residual hydrogen gas response intensity ΔVgres is reduced down to about 0.05 V by the normal post hydrogen annealing treatment. The wafer in-plane uniformity of the threshold voltages Vth is significantly improved by such a normal post hydrogen annealing treatment.

As a specific example, FIG. 7A illustrates a graph diagram for explaining the wafer in-plane distribution and the repeatability of the threshold voltages Vth. Here, it illustrates the wafer in-plane distributions of the threshold voltages Vth obtained after performing the normal post hydrogen annealing treatment to wafers whose sample numbers are #2 and #3. Regarding the wafer of #2, when a standard deviation of the dispersion of the threshold voltages Vth based on "the threshold voltage Vth=1.08 V" is represented as "σ", a relationship of "3σ=178 mV" is obtained so that the dispersion is very small, and therefore, the wafer is suitable for designing an interface circuit for taking out a sensor signal. Further, the variation in the threshold voltages Vth is reduced down to about half. The threshold voltages Vth of the wafer of #3 has also this relationship within the range of "3σ=178 mV", and therefore, the repeatability among the wafers is also improved.

FIG. 7B illustrates the wafer in-plane distribution of the hydrogen gas response intensities ΔVg of the sensor FET for the 1000-ppm air-diluted hydrogen. It is found that the hydrogen gas response intensities ΔVg also show excellent uniformity.

Note that the first embodiment describes the case that the hydrogen annealing treatment is performed at the temperature of 115° C. However, the anneal temperature is not limited to this temperature. While the diluted hydrogen gas is irradiated at an anneal temperature in a range of 80 to 300° C. depending on other conditions, a similar effect can be obtained.

Next, the means for solving the third problem will be explained.

As described above, in the catalytic-combustion-type hydrogen gas sensor, the sensor function and the heater function can be achieved by the same Pt wire. Therefore, by forming a temperature compensation element, the temperature of the sensor chip can be maintained constant even if the environmental temperature at which the hydrogen gas sensor is installed changes in a wide range from a low temperature of −50° C. to a high temperature of 70° C., and therefore, power supplied to the heater can be controlled. However, in the MISFE-type hydrogen gas sensor, it is difficult to use the MISFET itself as the heater, and therefore, it is difficult to use the MISFET as the temperature compensation element. Even if it is possible, the formation of the temperature compensation element is one of factors which prevent downsizing of the hydrogen gas sensor.

For the third problem, in order to maintain the temperature of the sensor chip at the set temperature when the environmental temperature at which the hydrogen gas sensor is installed changes in the wide range from the low temperature of about −50° C. to the high temperature of about 70° C., a method of controlling a consumption amount of the power consumption supplied to the heater wiring in response to the change of the environmental temperature at which the hydrogen gas sensor is installed is proposed instead of the method with the temperature compensation element.

The method of controlling the consumption amount of the power consumption supplied to the heater wiring in response to the change in the environmental temperature at which the sensor is installed will be explained with reference to FIGS. 8A and 8B. FIGS. 8A and 8B are a diagram of a control circuit and a graph diagram for explaining an operation (current-voltage characteristics) of the control circuit. FIG. 8A illustrates a heater resistor 82, a sensor FET 80, a power source voltage Vdd, and an enhancement-type control FET 81, which configure the hydrogen gas sensor according to the first embodiment.

As illustrated in FIG. 8A, the heater resistor 82 is connected to a source electrode of the control FET 81, and a drain electrode of the control FET 81 is connected to the power source voltage Vdd in series. If it is required to monitor a current or a voltage from the connection portion, a monitor terminal is connected. A source electrode of the sensor FET 80 is connected to a ground voltage, and a drain electrode thereof is connected to the power source voltage Vdd. A voltage is applied to a gate terminal 84 of the sensor FET 80 by a linear circuit such as an operational amplifier so that a source-drain current of the sensor FET 80 is at a constant value (a value by which the threshold voltage Vth is achieved) for change of the source-drain current depending on presence/absence of the hydrogen gas. Further, in the first embodiment, a current flowing through the heater resistor 82 is controlled by applying a voltage to a gate terminal 83 of the control FET 81 from an outside. Normally, a microcomputer is used for this control. A reason why the enhancement-type (normally-off-type) control FET is used as the control FET 81 is that, when a gate voltage Vg of the gate terminal 83 is 0 V, the control FET 81 is not turned on so as to have a high resistance, and a current does not practically flow through the heater resistor 82, which results in the power consumption of almost zero. In the first embodiment, the explanation is made with the n-channel type MISFET.

A resistance of the heater resistor 82 is R(Ts) at the sensor temperature of 115° C. That is, in consideration of the current "I"-voltage "V" characteristics of the heater resistor 82, a relationship of "I=V/R(Ts)" is obtained. As illustrated in FIG. 8B, by changing the gate voltage of the control FET 81 so that a straight line in the drawing is maintained constant, that is, a slope of the straight line is maintained constant, the current flowing through the heater resistor 82 can be controlled depending on the change of the temperature difference ΔT (change of the environmental temperature). In this manner, the operation temperature of 115° C. can be maintained constant by changing the power consumption. An intersection of the I-V characteristics of the control FET 81 with the relationship of "I=V/R(Ts)" indicates the actual current flowing through the heater resistor 82 and the actual voltage applied thereto. In FIG. 8B, a voltage obtained when the temperature difference ΔT is 150° C. is represented as "V(150)", and a voltage obtained when the temperature difference ΔT is 90° C. is represented as "V(90)". The changing of the gate voltage Vg applied to the control FET 81 can support a desired temperature difference ΔT. Practically, it is only required to monitor the current flowing through the heater resistor 82 or the voltage applied thereto, and therefore, feedback can be performed by measuring the resistance.

As described above, according to the first embodiment, when the temperature of the gate is set to 115° C. at the environmental temperature of −35° C., the temperature difference ΔT is 150° C., which results in relationships of "V(150)=2.74 V" and "I(ΔT=150° C.)=1.83 mA". When the current is continuously supplied to the heater wiring, even if the power consumption of 5 mW is required, the power consumption of 1.0 mW is achieved with the duty ratio of 1/5 (the heating for 6 seconds and the heating stop for 24 seconds), so that the operation for 1 year or longer can be achieved by a 3V-series cell.

As the method of achieving the structure that the region where the intrinsic FET region 35 does not overlap with the MEMS region 34 is formed to increase the thermal resistance of the insulation thin film covering the region, the first embodiment has described in detail the case that some through-holes 36 are formed in the insulation thin film in order to further increase the thermal resistance of the insulation thin film covering the region where the intrinsic FET region 35 does not overlap with the MEMS region 34. However, if the through-holes 36 are too large, the mechanical strength of the MEMS region 34 is deteriorated, and therefore, such a structure that the $Si_3N_4$ film forming the protective film 33 on the region where the intrinsic FET region 35 does not overlap with the MEMS region 34 is removed is effective because the thermal conductivity of the $Si_3N_4$ film forming the protective film 33 is one digit larger than the thermal conductivity of the $SiO_2$ film. In this case, in the bridge regions 90, 90S, 90G, and 90H, the $Si_3N_4$ film remains as the protective film as illustrated in FIGS. 3A and 3B.

In this case, while the reinforced region 91 is not provided, the closest distance between the edge of the intrinsic FET region 35 and the edge of the MEMS region 34 is formed so as to be 1 to 20 times the sum of widths of all the bridge regions. In the first embodiment, for example, by expanding the planar dimension of the MEMS region 34 to, for example, about 300 μm×300 μm, the power consumption characteristics similarly to that of the first embodiment can be achieved.

Note that, in the first embodiment, the lead-out wirings 20S, 20D, 20G, and 20H are made of the Al film. However, by forming them made of, for example, a Mo/Au/Mo stacked film, further high reliability can be obtained. Both of when the Mo/Au/Mo stacked film is used and when an Au/Mo stacked film is used, their thermal resistance equivalent to that of the Al film can be provided by adjusting their film thickness.

Further, in the first embodiment, the 4-pin Kovar-manufactured stem base (whose inner diameter is 4.22 ϕ) is used. However, it goes without saying that other mounting method is applicable. For example, mounting by four lead wires in a TO5 stem base is also possible. As a modified example of the stem structure, a stem base is used instead of a lead terminal connected to the source electrode is used, so that the stem base can be used with three lead terminals.

Further, in the first embodiment, the present invention has been explained by exemplifying the hydrogen gas sensor with using the Si-MISFET. However, the present invention is also applicable to a hydrogen gas sensor of other system such as a hydrogen gas sensor with a MIS-type capacitor.

(Second Embodiment)

The second embodiment relates to the second means for solving the first problem. The means according to the present second embodiment for solving the first problem will be explained below.

In the case of the MISFET-type hydrogen gas sensor, as different from a digital IC or an analog IC, there is little problem about an intrinsic performance of an element (a mutual conductance Gm, a source-drain current Ids which can be flown for each unit gate width, or others), a parasitic resistance Rsg between the source and the gate, or others. In consideration of this point, only a MISFET structure having repeatability is required, so that there is no need for using monocrystalline Si for the substrate. Since the matter that the thermal conductivity of Si crystal is too high, glass having a thermal conductivity significantly lower than that of monocrystalline Si is used for the substrate, and a hydrogen gas sensor is formed on the glass substrate, so that a hydrogen gas sensor with low power consumption can be achieved. For example, a sensor FET can be formed on a glass substrate by forming a channel layer made of polysilicon and a gate insulation film made of $SiO_2$ or others on the glass substrate, forming the Pt—Ti—O gate Si-MISFET similarly to the description in the above-described first embodiment, and removing polysilicon having a low thermal resistance existing on a portion except for the intrinsic FET region. In this case, the above-described Expression (1) can be satisfied even without the MEMS structure.

Next, a hydrogen gas sensor formed on the glass substrate according to the second embodiment by using a TFT (Thin Film Transistor) process will be explained in detail with reference to FIGS. 9 to 13. FIG. 9 is a cross-sectional view of a principal part of a sensor FET in which polysilicon formed on the glass substrate is used for the channel layer according to the second embodiment, FIGS. 10A to 10D are cross-sectional views of a principal part illustrating a method of manufacturing the sensor FET, FIG. 11 is a plan view of a principal part of a sensor chip, FIG. 12 is a cross-sectional schematic view of a hydrogen gas sensor on which the sensor chip is mounted, and FIG. 13 is a graph diagram for explaining heater power consumption characteristics of the hydrogen gas sensor. The TFT process is manufactured according to a low-temperature polysilicon TFT process used for a liquid crystal panel. Here, a step of forming a catalytic metal gate, a step of removing an insulation film on a gate electrode of a sensor FET, and a step of forming a heater portion will be mainly explained in detail.

Since the glass substrate is used as the substrate in the second embodiment, the MEMS structure is not provided. However, such an idea that the heater region is surrounded by a heat insulation structure remains. Further, in the second embodiment, WSi is used for the heater wiring. The resistivity of WSi at a temperature of 115° C. is, for example, 300 μΩcm.

A basic configuration of a hydrogen gas sensor according to the second embodiment and a method of manufacturing the same will be explained with reference to FIGS. 9 to 10D.

First, a heat-resistant foamed glass substrate (a substantially planar circular thin plate which is referred to as "glass wafer" at this stage) 13 is prepared, and $SiO_2$ is formed so as to have a thickness of, for example, 300 nm (omitted in FIG. 9) by a PECVD (Plasma Enhanced Chemical Vapor Deposition) method as a film for preventing contamination from this glass substrate 13. Next, an amorphous silicon (a-Si) film serving as a precursor is formed so as to have a thickness of, for example, 50 nm by the PECVD method, and, subsequently, hydrogen in the a-Si film is desorbed by a thermal annealing treatment at a temperature of 450° C. (dehydrogenating treatment). Next, laser beam having an energy density of 250 mJ/cm$^2$ is irradiated to the a-Si film by using a XeCl (308 nm) ultraviolet excimer laser annealing method so that a whole surface of the a-Si film is changed to a polysilicon layer. Next, the polysilicon layer except for the intrinsic FET region is removed by a photolithography method followed by a dry etching method. This remaining polysilicon layer becomes the channel layer 14.

Next, an insulation film ($SiO_2$) is formed so as to have a thickness of, for example, 40 nm by the PECVD method. After n$^+$-Si layers 15S and 15D are formed by doping P into regions serving as a source region and a drain region by an ion implantation method with using a photoresist as a mask, the ion-implanted impurity (P) is activated by an RTA (Rapid Thermal Annealing) method. Next, an insulation film ($SiO_2$ film) 16 is formed so as to have a thickness of, for example, 200 nm, and then, the insulation film 16 in the gate region is removed. Subsequently, a gate insulation film ($SiO_2$ film) 17 is formed so as to have a thickness of, for example, 40 nm by the PECVD method. Next, a Ti film, and then, a Pt film are formed so as to have thicknesses of, for example, 5 nm and 15 nm by an electron beam deposition method with using a photoresist as a mask, respectively, and then, a gate electrode 18 is formed by processing the Pt film and the Ti film by a lift-off method.

In this case, unless the formation from the channel layer 14 to the gate insulation layer 17 are continuously performed, a temporal change in FET characteristics is observed in some cases, and therefore, the continuous formation from the channel film 14 to the gate insulation film 17 is desired. An example of a manufacturing step of the continuous formation from the channel layer 14 to the gate insulation film 17 will be explained with reference to FIGS. 10A to 10D.

Figure 10A:
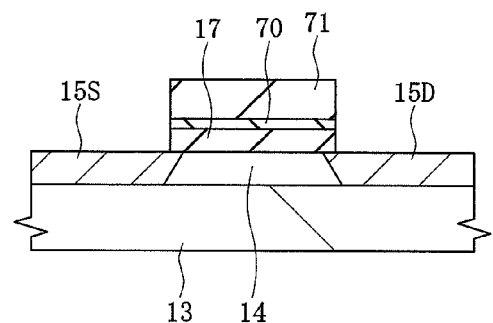

As illustrated in FIG. 10A, the a-Si film and the gate insulation film 17 are continuously formed, and a dummy-gate $Si_3N_4$ film 70 is formed so as to have a thickness of, for example, 40 nm. Subsequently, the $Si_3N_4$ film 70 and the gate insulation film 17 are sequentially removed with using a photoresist 71 as a mask, and then, the n$^+$-Si layers 15S and 15D are formed by doping P into the a-Si film by an ion implantation method.

Figure 10B:
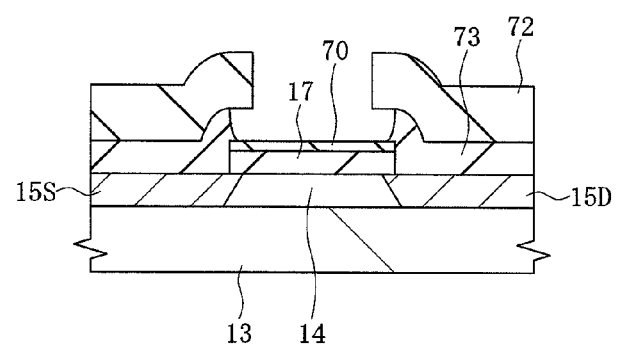

Next, as illustrated in FIG. 10B, the photoresist 71 is removed, and then, a $SiO_2$ film 73 is formed so as to have a thickness of, for example, 400 nm by the PECVD method.

Further, the ion-implanted impurities (P) into the a-Si film are activated by an RTA method. Subsequently, the $SiO_2$ film 73 in the gate region is removed with using a photoresist 72 as a mask by dry etching and wet etching with using BHF.

Figure 10C:
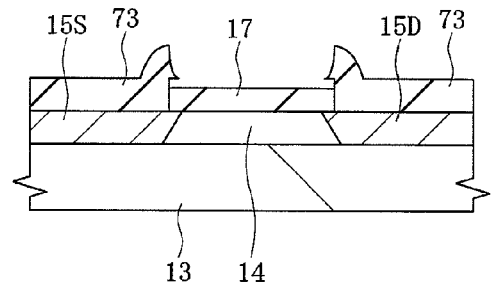

Next, as illustrated in FIG. 10C, the dummy-gate $Si_3N_4$ film 70 is removed by wet etching with phosphoric acid system, and then, the photoresist 72 is removed.

Figure 10D:
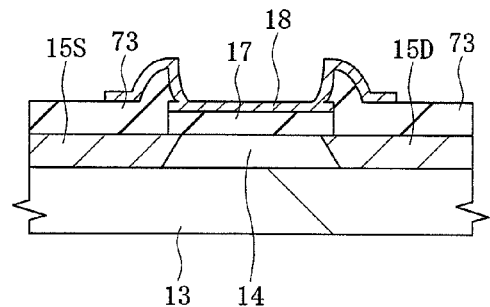

Next, as illustrated in FIG. 10D, a gate metal film is formed, and then, a gate electrode 18 is formed by using a lift-off gate resist of the gate metal. In the second embodiment, a width (gate length) of the gate region is, for example, 5 µm, and a gate width thereof is, for example, 15 µm.

Next, the gate electrode 18 is formed, and then, an insulation film ($SiO_2$ film) 19 is formed so as to have a thickness of, for example, 400 nm by the PECVD method. Next, a heater wiring 32P made of WSi is formed on the insulation film 19. A width of the heater wiring 32P is, for example, 1 µm, a height thereof is, for example, 0.1 µm, and a length thereof is, for example, 150 µm. Further, a resistivity of the heater wiring 32P at a temperature of 115° C. is 300 µΩcm. The heater wiring 32P is formed in an accordion-fold shape formed of three lines having a line interval of 1 µm therebetween based on a length unit of 25 µm. Its heater resistance at the temperature of 115° C. is 4.5 kΩ.

Next, a PSG protective film 30 for covering the heater wiring 32P is formed so as to have a thickness of, for example, 400 nm, and then, contact holes are bored in the PSG protective film 30, the insulation film 19, the gate insulation film 17, and the insulation film 16. Subsequently, a source electrode 11S and a drain electrode 11D are formed inside the contact holes, and besides, lead-out wirings are formed. Subsequently, a protective film 33 made of $Si_3N_4$ for covering the source electrode 11S, the drain electrode 11D, and the lead-out wirings is formed so as to have a thickness of 1 µm. The protective film 33, the PSG protective film 30, and the insulation film 19 on the gate electrode 18 of the sensor portion are removed by using dry etching and wet etching. Finally, in order to achieve the Pt—Ti—O gate structure, the air annealing treatment is performed at the temperature of 400° C. for 2 hours, and the temperature is returned to a room temperature, and then, the normal post hydrogen annealing treatment is performed with using the 0.1% air-diluted hydrogen at the temperature of 115° C. for 10 minutes. Then, the glass wafer is diced to, for example, 0.55-mm square dices to form the sensor chips. FIG. 11 illustrates a plan view of a principal part of a sensor chip 45S which has been substantially completed.

Then, as illustrated in FIG. 12, the sensor chip 45S is mounted on a stem base 51 equipped with four lead terminals as similarly to the above-described first embodiment.

A heat insulation material 501 obtained by processing a foamed glass (whose thermal conductivity is 0.061 W/(m·° C.)) into a rectangular parallelepiped shape having, for example, a planar dimension of "0.60 mm×0.60 mm" and a height of 3.5 mm is bonded onto a 4-pin Kovar-manufactured stem base 51 (whose inner diameter is 4.22 φ). A thickness of the sensor chip 45S is, for example, 500 µm, and a chip size (planar dimension) thereof is, for example, 0.55 mm×0.55 mm. As different from the above-described first embodiment, a shape of the source lead-out wiring 20S and a shape of the drain lead-out wiring 20D are different from each other. However, widths of the lead-out wirings 20S and 20D are, for example, 8 µm, and lengths thereof are, for example, 800 µm by adopting a zigzag structure (which is omitted in the drawing) or others. In this case, in order to reduce the thermal resistance, when a region edge of about 2 µm is formed on regions where the intrinsic FET region 35 and the lead-out wirings 20S, 20D, 20G and 20H are formed and when they are referred respectively to as "intrinsic FET region" and "lead-out wirings", the $Si_3N_4$ film of the protective film 33 except for these regions can be removed. In this case, there is no protective film on the gate region 25 for the sensor FET.

In such a hydrogen gas sensor, a total thermal resistance of four lead-out wirings 20S, 20D, 20G, and 20H is, for example, 2.78×10⁵ ° C./W, a resistance of the heater wiring 32P is, for example, 4.5 kΩ at the temperature of 115° C. At a power source voltage of 3 V, a current of 2 mA is flown, and the heater maximum power Powmax is 2 mW. The thermal resistance $R_D$ of the heat insulation material 501 made of the foamed glass is such large as 3.57×10⁵ ° C./W. In a case of a TFT-type Si-MISFET hydrogen gas sensor, a TFT substrate itself is also made of the foamed glass having a high thermal resistance, and therefore, a thermal resistance thereof from the heater region to the pad electrodes 40, 41, 42, and 43 is large, and the thermal resistance of 2.78×10⁵ ° C./W of the lead-out wirings 20S, 20D, 20G, and 20H largely contributes to the thermal resistance between the heater region and the pad electrodes 40, 41, 42, and 43.

FIG. 13 illustrates a graph diagram for explaining a relationship between the resistance of the heater wiring and the power consumption obtained when the current is flown through the heater wiring. As illustrated in FIG. 13, operation with a power consumption of 1.7 mV (a current of 0.615 mA and a voltage of 2.764 V) at an operation temperature of 115° C. which achieves the temperature difference ΔT=150° C. is possible.

As described above, the hydrogen gas sensor exemplified in the second embodiment has the relationships of "$1/R_D$=0.28×10⁻⁵ W/° C.", "$1/R_L$=0.269×10⁻⁵ W/° C.", and "$4\pi\lambda r_A$=0.512×10⁻⁵ W/° C.", and therefore, the "Powmax/ΔTmax" in the left-hand side of the Expression (1) becomes 1.113×10⁻⁵ W/° C., which satisfies the Expression (1).

Note that, if the power consumption is sacrificed to some extent, the TFT sensor can be formed with using quartz glass instead of the heat-resistant foamed glass substrate.

As described above, according to the second embodiment, the hydrogen gas sensor is formed on the glass substrate having a thermal conductivity significantly lower than that of the monocrystalline Si, and therefore, the thermally-insulating characteristics are extremely excellent, and a hydrogen gas sensor having low power consumption can be achieved. Further, since the glass substrate is used, the hydrogen gas sensor can also be applied to a radioactive environment such as a hydrogen gas sensor for a nuclear reactor exhaust gas or space. Further, since it is not required to use the MEMS structure as different from the case of using the Si substrate, the hydrogen gas sensor can be manufactured at a low cost.

(Third Embodiment)

In the third embodiment, an example of a hydrogen gas sensor having the power source voltage of 3 V and the Powmax of 11.7 mW equipped with a heater wiring formed of an Al film to which Si is doped will be explained with reference to FIGS. 14 and 15. The maximum value of the current flowing through the heater wiring is 3.9 mA. FIGS. 14 and 15 are a cross-sectional view of a principal part of a sensor FET and a plan view of a principal part of a sensor chip, respectively. The sensor chip is manufactured by using a SOI substrate similarly to the above-described first embodiment. As a heater wiring 32A, a Si-doped Al film having a resistivity of 4 µΩcm at a temperature of 115° C. is used, and a width thereof is, for example, 1 µm, a height thereof is, for example, 0.5 µm, and a length thereof is, for example, about 9.6 mm. A planar dimension of an intrinsic FET region 35 is, for example, 170 µm×150 µm, a planar dimension of the heater region is, for example, 160 µm×130 µm, and the heater wiring 32A formed of the Si-doped Al film having a thickness of 160 µm is formed so as to form 60 lines. A chip size (planar dimension) of the sensor chip 45 is, for example, 1 mm×1 mm. That of the MEMS region 34 is, for example, 300 µm×300 µm. Widths of the lead-out wirings 20S, 20D, 20G, and 20H are, for example, 20 µm, and lengths thereof are, for example, about 700 µm. A gate length of the sensor FET is, for example, 5 µm, and a gate width thereof is, for example, 150 µm. In the present third embodiment, the number of the folded wirings is large, and therefore, the heater wiring 32A is partially omitted in FIGS. 14 and 15.

A heat insulation material obtained by processing a foamed glass (whose thermal conductivity is 0.061 W/(m·° C.)) into a rectangular parallelepiped shape having, for example, a planar dimension of 1 mm×1 mm and a height of 3.0 mm is used, and this heat insulation material is bonded to a stem base similarly to FIG. 4A described in the above-described first embodiment. Since the heater wiring 32A has a resistant value of 768Ω at a chip temperature of 115° C., the maximum power consumption Powmax at the chip temperature of 115° C. is 11.7 mW. Since the planar dimension of the MEMS region 34 is, for example, 300 µm×300 µm, and since the planar dimension of the intrinsic FET region 35 is, for example, 170 µm×150 µm, the closest distance between the edge of the intrinsic FET region 35 and the edge of the MEMS region 34 in the third embodiment is, for example, 65 µm, which is formed about 1.8 times larger than 36 µm (6 µm×6 lines) which is the sum of the widths of all the bridge regions and the widths of all the reinforced region.

As described above, the hydrogen gas sensor exemplified in the third embodiment has the relationships of "$1/R_D=2.04\times 10^{-5}$ W/° C.", "$1/R_L=1.06\times 10^{-5}$ W/° C.", and "$4\pi\lambda r_A=3.30\times 10^{-5}$ W/° C.", and therefore, the sum of three terms becomes $6.4\times 10^{-5}$ W/° C.", and the "Powmax/ΔTmax" in the left-hand side of the Expression (1) becomes $6.7\times 10^{-5}$ W/° C., which satisfies the Expression (1).

Further, an example of a hydrogen gas sensor having the power source voltage of 3 V and the Powmax of 11.7 mW equipped with a heater wiring formed of a Si-doped Al film having a double-layer structure will be explained with reference to FIGS. 16 and 17. The current flowing through the heater wiring is 3.9 mA. FIGS. 16 and 17 are a cross-sectional view of a principal part of a sensor FET and a plan view of a principal part of a sensor chip, respectively. Similarly to the above-described first embodiment, the sensor chip is manufactured by using a SOI substrate. As heater wirings 32A and 322, a Si-doped Al film having a resistivity of 4 µΩcm at a temperature of 115° C. is used, and widths thereof are, for example, 1 µm, heights thereof are, for example, 0.5 µm, and lengths thereof are, for example, about 9.6 mm. A planar dimension of the intrinsic FET region 35 is, for example, 110 µm×130 µm, a planar dimension of the heater region is, for example, 100 µm×110 µm, and the heater wirings 32A and 322 formed of the Si-doped Al film having a thickness of 100 µm are formed so as to form a double layer with 48 lines. In the present third embodiment, the number of the folded wirings is large, and therefore, parts of the heater wirings 32A and 322 are omitted in FIG. 16. In FIG. 17, the heater wiring 32 of the upper layer is omitted. A chip size (planar dimension) of the sensor chip 45 is, for example, 1 mm×1 mm. That of the MEMS region 34 is, for example, 200 µm×220 µm. Widths of the lead-out wirings 20S, 20D, 20G, and 20H are, for example, 20 µm, and lengths thereof are, for example, about 700 µm. A gate length of the sensor FET is, for example, 5 µm, and a gate width thereof is, for example, 90 µm. The thin-film structure of the bridge region is the same as that of the above-described first embodiment except for the different point in the dimension. Since the planar dimension of the MEMS region 34 is, for example, 200 µm×220 µm, and since the planar dimension of the intrinsic FET region 35 is, for example, 110 µm×130 µm, the closest distance between the edge of the intrinsic FET region 35 and the edge of the MEMS region 34 in the third embodiment is, for example, 45 µm, which is formed about 1.25 times larger than 36 µm (6 µm×6 lines) which is the sum of the widths of all the bridge regions and the widths of all the reinforced region.

A heat insulation material obtained by processing a foamed glass (whose thermal conductivity is 0.061 W/(m·° C.)) into a rectangular parallelepiped shape having, for example, a planar dimension of 1 mm×1 mm and a height of 3.0 mm is used, and this heat insulation material is bonded to a stem base similarly to FIG. 4A described in the above-described first embodiment. Since the heater wirings 32A have a resistant value of 768Ω at a chip temperature of 115° C., it is found that the power consumption at the chip temperature of 115° C. is 11.7 mW. Although the detailed description is omitted, the relationship satisfies the Expression (1).

As described above, according to the third embodiment, even if the heater wiring is made of the Si-doped Al film without using WSi, a hydrogen gas sensor which can be operated for one year or longer while the power consumption is slightly high can be manufactured by using the intermittent operation such as a duty ratio of 0.08 (heating for 2.4 seconds and heating stop for 27.6 seconds).

(Fourth Embodiment)

The fourth embodiment relates to the means for solving the third problem. In order to maintain the temperature of the sensor chip at the set temperature when the environmental temperature at which the hydrogen gas sensor is installed changes in the wide range from the low temperature of about −50° C. to the high temperature of about 70° C., the above-described first embodiment has explained the method of controlling the consumption amount of the power consumption supplied to the heater wiring in response to the change of the environmental temperature at which the sensor is installed with reference to FIGS. 8A and 8B instead of the method with the temperature compensation element. In a sensor chip according to the fourth embodiment, the enhancement-type control FET 81 explained in the above-described first embodiment is formed on the SOI substrate outside the MEMS region 34.

FIG. 18 illustrates a plan view of a principal part of the sensor chip according to the fourth embodiment. In the fourth embodiment, when the sensor FET 80 is formed in the manufacturing of the control FET 81, the step of removing the insulation film on the gate electrode is omitted. However, the air annealing treatment at the temperature of 400° C. for 2 hours followed by the normal post hydrogen annealing treatment are performed immediately after the gate electrode is formed, and then, the insulation film is formed. FIG. 18 illustrates a heater resistor 82, a sensor FET 80, and an enhancement-type control FET 81. The heater resistor 82 is connected to a source electrode of the control FET 81, and a drain electrode of the control FET 81 is connected to a pad electrode 40 having the power source of Vdd in series. When it is required to monitor a voltage from a connection portion between the heater resistor 82 and the source electrode of the control FET 81, a monitor terminal is connected to the connection portion. However, the monitor terminal is not manufactured in the fourth embodiment. It illustrates a pad electrode 42 connected to the source electrode of the sensor FET 80, a pad electrode 41 connected to a gate electrode of the control FET 81, and a pad electrode 43 connected to a gate electrode of the sensor FET 80. A threshold voltage Vth of the control FET 81 is, for example, 1.0 V, a gate length thereof is, for example, 2 µm, and a gate width thereof is, for example, 100 µm. When a source-drain voltage Vds is 0.2614 V, a source-drain current is 1.826 mA. That is, the gate voltage is selected to be positioned at an intersection between the I-V characteristics of the control FET 81 and the "I=V/R(Ts)" at V(150) in FIG. 8B described above.

The control FET 81 is manufactured close to the pad electrode outside the MEMS region 34 so that the temperature of the heater region is difficult to affect thereon.

As described above, according to the fourth embodiment, the control FET 81 for controlling the power consumption of the heater region is configured as an IC, and therefore, it can be easily connected to an analog circuit such as an operational amplifier IC, and the operation temperature of the hydrogen gas sensor can be easily maintained constant against the change of the environmental temperature.

(Fifth Embodiment)

A flammable gas sensor to which a tin oxide film ($SnO_2$ film) according to a fifth embodiment is applied will be explained with reference to FIGS. 19 and 20.

In the fifth embodiment, different points from the above-described first embodiment will be mainly explained. FIGS. 19 and 20 are a cross-sectional view of a sensor chip portion obtained when a polysilicon film is used for the heater wiring, and a plan view of a principal part of the sensor chip, respectively. Similarly to the above-described first embodiment, the sensor chip is manufactured with using the SOI substrate. As a heater wiring 32PP, a polysilicon film having a resistivity of 450 µΩcm at a temperature of 400° C. is used, and a width thereof is, for example, 1 µm, a height thereof is, for example, 0.5 µm, a length thereof is, for example, about 100 µm, and has a resistance value of 900Ω. A planar dimension of the heater region is, for example, 25 µm×20 µm.

In a sensor chip 45 according to the fifth embodiment, first, a Si layer 24PP and a thermal oxidation film ($SiO_2$ film) 26PP are sequentially formed on an embedded insulation layer 23. A thickness of the Si layer 24PP is, for example, 0.2 µm. Further, a polysilicon film 32PP is formed on the thermal oxidation film 26PP. A thickness of the polysilicon film 32PP is, for example, 0.5 µm. Subsequently, P is doped into the heater region by an ion implantation method, and then, the polysilicon film 32PP is processed in accordance with the heater wiring. Subsequently, a PSG protective film 30 for covering the polysilicon film 32PP is formed so as to have a thickness of, for example, 300 nm, and then, the polysilicon film 32PP is activated by an annealing treatment. Then, the PSG protective film 30 on the sensor region 100 is removed, and a tin oxide film ($SnO_2$ film) 101 is formed by a sputtering method and is further processed. Then, lead-out wirings 20a, 20b, 20c, and 20d made of Al are formed, and a protective film 33 formed of the PSG protective film 30 and a $Si_3N_4$ film is formed similarly to the above-described first embodiment.

While the temperature characteristics are different, the heater wiring formed of the polysilicon film 32PP has a resistance value of 900 Ω at a temperature of 400° C., so that the power consumption of 10 mW can be obtained in the operation at the temperature of 400° C. by applying the same mounting method as the method explained with reference to FIG. 4A in the above-described first embodiment. The usage of the through-holes 36 in the bridge regions, the reinforced regions 91, the lead-out wirings 20a, 20b, 20c, and 20d is similar to that in the above-described first embodiment. A chip size (planar dimension) of the sensor chip 45 is, for example, 0.45 mm×0.45 mm. A heat insulation material obtained by processing a foamed glass (whose thermal conductivity is 0.061 W/(m·° C.)) into a rectangular parallelepiped shape having, for example, a planar dimension of 0.5 mm×0.5 mm and a height of 4.0 mm is used, and this heat insulation material is bonded to a stem base similarly to FIG. 4A described in the first embodiment.

As described above, according to the fifth embodiment, it is found that the present invention is also effective to the flammable gas sensor to which the tin oxide film ($SnO_2$ film) 101 is applied. Note that, in the fifth embodiment, the control FET is formed on the same substrate similarly to the above-described fourth embodiment, so that the current flowing through the heater wiring can be controlled.

In the foregoing, the invention made by the present inventor has been concretely described based on the embodiments. However, it is needless to say that the present invention is not limited to the foregoing embodiments and various modifications and alterations can be made within the scope of the present invention.

For example, in the above-described first to fifth embodiments, the Mo/Au/Mo wiring can be applied to the lead-out wirings, so that further high reliability can be obtained. Further, as the mounting structure, the embodiments in which the heat insulation material made of the foamed glass is used have been explained. However, even if the PEEK material having the thickness of, for example, 3 mm is used, the Expression (1) can be satisfied while the power consumption is slightly large.

Further, in the above-described first to fifth embodiments, the sensor FET in respond to a target gas has been described as the present invention. A sensitivity thereof can be increased by the method of detecting the difference of the sensor signals achieved by forming the structure similar to those of the above-described first to fourth embodiments, forming the reference sensor by covering the gate portion with the protective film made of $SiO_2$, PSG, $Si_3N_4$ or others, and using this reference sensor (FET) mounted in accordance with each of the first to fourth embodiments and the sensor FET explained previously. In this case, the reference sensor can be achieved by using the process of forming the gate electrode, and then, performing the air annealing treatment thereto at the temperature of 400° C. for 2 hours followed by the normal hydrogen annealing treatment, and then, forming the insulation film on the gate electrode.

Further, in the above-described first to fourth embodiments, the explanation has been made with the n-channel-type MISFET. However, it goes without saying that the present invention can be implemented by adopting a p-channel-type MISFET and reversing a polarity thereof.

INDUSTRIAL APPLICABILITY

The present invention can be applied to a gas sensor which detects not only a hydrogen gas but also various flammable gases.

SYMBOL EXPLANATION

8 lead wire
9 sensor chip
10 heater region
11S source electrode
11D drain electrode
13 glass substrate
14 channel layer
15S and 15D $n^+$-Si layer
16 insulation film ($SiO_2$ film)
17 gate insulation film ($SiO_2$ film)
18 gate electrode 19 insulation film (SiO$_2$ film)
20a, 20b, 20c, 20d, 20D, 20G, 20H, and 20S lead-out wiring
20Z lead-out wiring in bridge region
20ZS lead-out wiring
22 Si substrate
23 embedded insulation layer (SiO$_2$ film)
24 channel layer (Si layer)
24PP Si layer
25 gate region
26 local oxidation film (SiO$_2$ film)
26PP thermal oxidation film (SiO$_2$ film)
27 gate insulation film (SiO$_2$ film)
28 gate electrode (Pt—Ti—O gate, catalytic metal gate)
28S and 28D n$^+$-Si layer
29 and 30 PSG protective film
31S source electrode
31D drain electrode
32, 32A, and 32P heater wiring
32PP polysilicon film (heater wiring)
33, 33S, and 33SS protective film
34 MEMS region
35 intrinsic FET region
36 through-hole
37 contact hole
40, 41, 42, and 43 pad electrode
44G, 44H, and 44S contact hole
45 and 45S sensor chip
50 heat insulation material
51 stem base
54 flange of stem base
55 lead terminal
56 cap
57 PEEK material
58 water-proof permeable material
59 cap size
60 intake hole
61 glass material
70 Si$_3$N$_4$ film
71 and 72 photoresist
73 SiO$_2$ film
80 sensor FET
81 control FET
82 heater resistor
83 gate terminal of control FET
84 gate terminal of sensor FET
90, 90S, 90G, 90H, 95, and 96 bridge region
91 reinforced region
93 and 93SS stacked film
100 sensor region
101 tin oxide film (SnO$_2$ film)
322 heater wiring
501 heat insulation material

The invention claimed is:
1. A gas sensor comprising: a sensor chip including a sensor MISFET and a heater formed at a heater region on a main surface of a substrate; a mounting substrate on which the sensor chip is mounted; and a heat insulation material inserted between the sensor chip and the mounting substrate,
wherein, on the main surface of the substrate of the sensor chip, a pad electrode is formed so as to be connected to the heater via a lead-out wiring, a lead terminal used for connection to an outside is formed so as to penetrate through the mounting substrate, and the pad electrode and the lead terminal are connected to each other by a lead wire,
wherein the sensor MISFET includes a catalytic metal gate, a source electrode, and a drain electrode, and the heater is arranged on a plane that extends between the source electrode and the drain electrode and has a first portion at one side of the catalytic metal gate and a second portion at an opposite side of the catalytic metal gate and has a gap region between the first portion and the second portion, and the heater is provided at a height position higher than a height position of the catalytic metal gate in a direction perpendicular to the plane on which the heater is arranged,
and wherein a thermal resistance obtained from the heater region where the heater is formed to the mounting substrate so as to interpose the sensor chip and the heat insulation material therebetween is represented as "$R_D$", a total thermal resistance of a thermal resistance from the heater region to the pad electrode and a thermal resistance of the lead wire is represented as "$R_L$", a radius of a circle having the same area size as a surface area of the heater region is represented as "$r_A$", a thermal conductivity of atmosphere gas generated by the heating of the heater is represented as "$\lambda$", a difference between a set temperature of the heater region and an environmentally-assumed lowest temperature in installation is represented as a temperature difference "$\Delta T_{max}$", and a heater maximum power supplied to the heater which is determined by an electric resistance of the heater at the set temperature and a power source voltage is represented as "Powmax", to provide a heater maximum power Powmax of 25 mW or less, but greater than zero, throughout a specified operation range of the gas sensor, the thermal resistances $R_D$ and $R_L$ and the surface area of the heater region are set so as to satisfy a relationship of "Powmax/$\Delta T_{max} > 1/R_D + 1/R_L + 4\pi\lambda \cdot r_A$".

2. The gas sensor according to claim 1,
wherein, the heating time of the heater and heating stop time of the heater are represented as "$\tau_1$" and "$\tau_2$", respectively, and a relationship of "duty ratio $=\tau_1/(\tau_1+\tau_2)$" is in a range of 1/14 to 1.0.

3. The gas sensor according to claim 1,
wherein the heat insulation material is made of foamed glass or PEEK material.

4. The gas sensor according to claim 1,
wherein the heater is made of WSi, polysilicon, Al, or W.

5. The gas sensor according to claim 1,
wherein the substrate of the sensor chip is a SOI substrate formed of a Si substrate, an embedded insulation layer, and a Si layer, and the sensor MISFET is formed in a MEMS region where the Si substrate of the SOI substrate is bored.

6. The gas sensor according to claim 1,
wherein the substrate of the sensor chip is a SOI substrate formed of a Si substrate, an embedded insulation layer, and a Si layer, and the heater region where a heater wiring of the heater is arranged so as to sandwich a catalytic region including two lead wires is formed in a MEMS region where the Si substrate of the SOI substrate is bored.

7. The gas sensor according to claim 1,
wherein the substrate of the sensor chip is a glass substrate.

8. The gas sensor according to claim 1,
wherein the substrate of the sensor chip is a SOI substrate formed of a Si substrate, an embedded insulation layer, and a silicon layer, and the SOI substrate includes: a MEMS region where the Si substrate is bored; and an intrinsic FET region where the sensor MISFET is formed inside the MEMS region and which has a smaller planar area size than that of the MEMS region, a lead-out wiring is formed for connecting the catalytic metal gate of the sensor MISFET, the source electrode thereof, the drain electrode thereof, and one end of the heater to a plurality of the pad electrodes provided outside the MEMS region, respectively, a part of the MEMS region which does not overlap with the intrinsic FET region includes: bridge regions where the lead-out wiring and a protective film for covering the lead-out wiring are formed on the embedded insulation layer; and reinforced regions where only the protective film is formed on the embedded insulation layer, a part of the MEMS region which does not overlap with the intrinsic FET region and except for the bridge regions and the reinforced regions includes a through-hole where the protective film and the embedded insulation layer are removed, and the closest distance between an edge of the intrinsic FET region and an edge of the MEMS region is 1 to 20 times the sum of widths of all the bridge regions and widths of all the reinforced regions.

9. The gas sensor according to claim 8,
wherein the protective film includes: a first insulation film which is a lower layer made of silicon oxide; and a second insulation film which is an upper layer made of silicon nitride, and the intrinsic FET region except for a gate region where the catalytic metal gate is formed is covered with the first and second insulation films, the bridge regions are covered with the first and second insulation films, and the reinforced regions are covered with only the first insulation film.

10. The gas sensor according to claim 1,
wherein the substrate of the sensor chip is a SOI substrate formed of a Si substrate, an embedded insulation layer, and a silicon layer, and the SOI substrate includes: a MEMS region where the Si substrate is bored; and an intrinsic FET region where the sensor MISFET is formed inside the MEMS region and which has a smaller planar area size than that of the MEMS region, a lead-out wiring is formed for connecting the catalytic metal gate of the sensor MISFET, the source electrode thereof, the drain electrode thereof, and one end of the heater to a plurality of the pad electrodes provided outside the MEMS region, respectively, a part of the MEMS region which does not overlap with the intrinsic FET region includes: bridge regions where the lead-out wiring and a protective film for covering the lead-out wiring are formed on the embedded insulation layer; and reinforced regions where only the protective film is formed on the embedded insulation layer, and the protective film includes: a first insulation film which is a lower layer made of silicon oxide; and a second insulation film which is an upper layer made of silicon nitride, and the protective film of the part of the MEMS region which does not overlap with the intrinsic FET region and except for the bridge regions is formed of only the first insulation film.

11. The gas sensor according to claim 10,
wherein a part of the MEMS region which does not overlap with the intrinsic FET region and except for the bridge regions and the reinforced regions includes a through-hole which penetrates through the embedded insulation layer, and the closest distance between an edge of the intrinsic FET region and an edge of the MEMS region is 1 to 20 times the sum of widths of all the bridge regions and widths of all the reinforced regions.

12. The gas sensor according to claim 1,
wherein four of the pad electrode are formed on the main surface of the substrate of the sensor chip, and the catalytic metal gate of the sensor MISFET, the source electrode thereof, the drain electrode thereof, and one end of the heater are connected to the four of the pad electrode via a lead-out wiring, respectively, and the source electrode of the sensor MISFET and another end of the heater are electrically connected to each other.

13. The gas sensor according to claim 1,
wherein the catalytic metal gate of the sensor MISFET has a structure due to annealing under hydrogen atmosphere gas.

14. The gas sensor according to claim 13,
wherein the hydrogen atmosphere gas is air-diluted gas, and an annealing temperature is in a range of 80 to 300° C.

15. The gas sensor according to claim 13,
wherein the catalytic metal gate is made of Pt—Ti—O.

16. A gas sensor comprising: a sensor chip including a sensor MISFET, a control MISFET, and a heater at a heater region formed on a main surface of a substrate; a mounting substrate on which the sensor chip is mounted; and a heat insulation material inserted between the sensor chip and the mounting substrate, wherein the sensor MISFET includes a catalytic metal gate, a source electrode, and a drain electrode, and the heater is arranged on a plane that extends between the source electrode and the drain electrode and has a first portion at one side of the catalytic metal gate and a second portion at an opposite side of the catalytic metal gate and has a gap between the first portion and the second portion, and the heater is provided at a height position higher than a height position of the catalytic metal gate in a direction perpendicular to the plane on which the heater is arranged, wherein one end of the heater is connected to the source electrode of the control MISFET, another end of the heater and the source electrode of the sensor MISFET are grounded, and a drain electrode of the control MISFET and the drain electrode of the sensor MISFET are connected to a power source, wherein, on the main surface of the substrate of the sensor chip, a pad electrode is formed so as to be connected to the heater via a lead-out wiring, a lead terminal used for connection to an outside is formed so as to penetrate through the mounting substrate, and the pad electrode and the lead terminal are connected to each other by a lead wire, and, wherein a thermal resistance obtained from the heater region where the heater is formed to the mounting substrate so as to interpose the sensor chip and the heat insulation material therebetween is represented as "$R_D$", a total thermal resistance of a thermal resistance from the heater region to the pad electrode and a thermal resistance of the lead wire is represented as "$R_L$", a radius of a circle having the same area size as a surface area of the heater region is represented as "$r_A$", a thermal conductivity of atmosphere gas generated by the heating of the heater is represented as "$\lambda$", a difference between a set temperature of the heater region and an environmentally-assumed lowest temperature in installation is represented as a temperature difference "αTmax", and a heater maximum power supplied to the heater which is determined by an electric resistance of the heater at the set temperature and a power source voltage is represented as "Powmax", to provide a heater maximum power Powmax of 25 mW or less but greater than zero throughout a specified operation range of the gas sensor, the thermal resistances $R_D$ and $R_L$ and the surface area of the heater region are set so as to satisfy a relationship of "Powmax/$\Delta$Tmax>$1/R_D+1/R_L+4\pi\lambda\cdot r_A$".

17. A gas sensor comprising: a sensor chip including a sensor MISFET, a control MISFET, and a heater at a heater region formed on a main surface of a substrate; a mounting substrate on which the sensor chip is mounted; and a heat insulation material inserted between the sensor chip and the mounting substrate,
- wherein the sensor MISFET includes a catalytic metal gate, a source electrode, and a drain electrode, and the heater is arranged on a plane that extends between the source electrode and the drain electrode and has a first portion at one side of the catalytic metal gate and a second portion at an opposite side of the catalytic metal gate and has a gap between the first portion and the second portion, and the heater is provided at a height position higher than a height position of the catalytic metal gate in a direction perpendicular to the plane on which the heater is arranged,
- wherein one end of the heater is connected to a source electrode of the control MISFET, another end of the heater and a source electrode of the sensor MISFET are grounded, and a drain electrode of the control MISFET and a drain electrode of the sensor MISFET are connected to a power source,
- wherein the control MISFET is an enhancement-type MISFET,
- wherein, on the main surface of the substrate of the sensor chip, a pad electrode is formed so as to be connected to the heater via a lead-out wiring, a lead terminal used for connection to an outside is formed so as to penetrate through the mounting substrate, and the pad electrode and the lead terminal are connected to each other by a lead wire, and,
- wherein a thermal resistance obtained from the heater region where the heater is formed to the mounting substrate so as to interpose the sensor chip and the heat insulation material therebetween is represented as "$R_D$", a total thermal resistance of a thermal resistance from the heater region to the pad electrode and a thermal resistance of the lead wire is represented as "$R_L$", a radius of a circle having the same area size as a surface area of the heater region is represented as "$r_A$", a thermal conductivity of atmosphere gas generated by the heating of the heater is represented as "$\lambda$", a difference between a set temperature of the heater region and an environmentally-assumed lowest temperature in installation is represented as a temperature difference "$\Delta$Tmax", and a heater maximum power supplied to the heater which is determined by an electric resistance of the heater at the set temperature and a power source voltage is represented as "Powmax", to provide a heater maximum power Powmax of 25 mW or less but greater than zero throughout a specified operation range of the gas sensor, the thermal resistances $R_D$ and $R_L$ and the surface area of the heater region are set so as to satisfy a relationship of "Powmax/$\Delta$Tmax>$1/R_D+1/R_L+4\pi\lambda\cdot r_A$".

18. A sensor for the detection of flammable gas, comprising a sensor chip including a field effect transistor for the sensor and a heater wiring formed at a heater region on a main surface of a substrate; a mounting substrate on which the sensor chip is mounted; and a heat insulation material inserted between the sensor chip and a mounting substrate,
- wherein, on the main surface of the substrate of the sensor chip, a pad electrode is formed so as to be connected to the heater via a lead-out wiring, a lead terminal used for connection to an outside is formed so as to penetrate through the mounting substrate, and the pad electrode and the lead terminal are connected to each other by a lead wire,
- wherein the field effect transistor for the sensor includes a catalytic metal gate, a source electrode, and a first drain electrode, and
- the heater wiring is arranged on a plane that extends between the source electrode and the drain electrode and has a first portion at one side of the catalytic metal gate and a second portion at an opposite side of the catalytic metal gate and has a gap between the first portion and the second portion, and the heater wiring is provided at a height position higher than a height position of the catalytic metal gate of the field effect transistor in a direction perpendicular to the plane on which the heater wiring is arranged,
- and wherein a thermal resistance obtained from the heater region where the heater is formed to the mounting substrate so as to interpose the sensor chip and the heat insulation material therebetween is represented as "$R_D$", a total thermal resistance of a thermal resistance from the heater region to the pad electrode and a thermal resistance of the lead wire is represented a "$R_L$", a radius of a circle having the same area as a surface area of the heater region is represented as "$r_A$", a thermal conductivity of atmosphere gas generated by the heating of the heater is represented as "$\lambda$", a difference between a set temperature of the heater region and an environmentally-assumed lowest temperature in installation is represented as a temperature difference "$\Delta$Tmax", and a heater maximum power supplied to the heater which is determined by an electric resistance of the heater at the set temperature and a power source voltage is represented as "Powmax", to provide heater maximum Power Powmax of 25 mW or less, but greater than zero, throughout a specified operation range of the gas sensor, the thermal resistances $R_D$ and $R_L$ and the surface area of the heater region are set so as to satisfy a relationship of "Powmax/$\Delta$Tmax>$1/R_D+1/R_L+4\pi\lambda\cdot r_A$".

\* \* \* \* \*